(12) United States Patent
Holton et al.

(10) Patent No.: US 11,812,983 B2
(45) Date of Patent: *Nov. 14, 2023

(54) FORCEPS WITH TWO-PART DRIVE BAR

(71) Applicant: GYRUS ACMI, INC., Westborough, MA (US)

(72) Inventors: Jeffrey D. Holton, Stanchfield, MN (US); Theodore C. Blus, Arden Hills, MN (US); Mark Kroll, Dresser, WI (US); John Mensch, Plymouth, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/808,258

(22) Filed: Jun. 22, 2022

(65) Prior Publication Data

US 2022/0361904 A1    Nov. 17, 2022

Related U.S. Application Data

(63) Continuation of application No. 16/829,799, filed on Mar. 25, 2020, now Pat. No. 11,406,408.

(Continued)

(51) Int. Cl.
*A61B 17/29* (2006.01)
*A61B 17/295* (2006.01)
(Continued)

(52) U.S. Cl.
CPC ........ *A61B 17/282* (2013.01); *A61B 17/1285* (2013.01); *A61B 17/2804* (2013.01);
(Continued)

(58) Field of Classification Search
CPC ........ A61B 17/2912; A61B 2017/2932; A61B 2017/2933; A61B 2017/2936;
(Continued)

(56) References Cited

U.S. PATENT DOCUMENTS 6,458,130 B1    10/2002   Frazier et al.
7,131,971 B2    11/2006   Dycus et al.
(Continued)

OTHER PUBLICATIONS

U.S. Appl. No. 16/829,799, U.S. Pat. No. 11,406,408, filed Mar. 25, 2020, Forceps With Two-Part Drive Bar.
(Continued)

*Primary Examiner* — Majid Jamialahmadi
(74) *Attorney, Agent, or Firm* — Schwegman Lundberg & Woessner, P.A.

(57) ABSTRACT

A forceps having a first jaw and a second jaw, where at least one of the first and second jaws is capable of moving between an open position and a closed positions. The forceps including an inner shaft located within an outer shaft and extending along the longitudinal axis, and a drive bar coupled to and extending distally from the inner shaft. The drive bar including a pair of drive bar struts extending from a distal portion of the inner shaft and positioned laterally inward of at least one of first and second set of flanges of the first and second jaws. A drive pin is securable to the pair of drive bar struts and the drive bar is translatable within the outer shaft to translate the drive pin to move the first jaw and/or the second jaw between open and closed positions.

19 Claims, 12 Drawing Sheets

Related U.S. Application Data

(60) Provisional application No. 62/994,220, filed on Mar. 24, 2020, provisional application No. 62/841,476, filed on May 1, 2019, provisional application No. 62/826,522, filed on Mar. 29, 2019, provisional application No. 62/826,532, filed on Mar. 29, 2019.

(51) Int. Cl.
| | | |
|---|---|---|
| *A61B 17/28* | (2006.01) | |
| *A61B 18/14* | (2006.01) | |
| *A61B 17/128* | (2006.01) | |
| *A61B 90/00* | (2016.01) | |
| *A61B 17/285* | (2006.01) | |
| *B23K 26/21* | (2014.01) | |
| *A61B 17/32* | (2006.01) | |
| *A61B 18/00* | (2006.01) | |

(52) U.S. Cl.
CPC ........ *A61B 17/285* (2013.01); *A61B 17/2833* (2013.01); *A61B 17/2909* (2013.01); *A61B 18/149* (2013.01); *A61B 18/1445* (2013.01); *A61B 90/03* (2016.02); *B23K 26/21* (2015.10); *A61B 17/29* (2013.01); *A61B 17/295* (2013.01); *A61B 18/1442* (2013.01); *A61B 18/1447* (2013.01); *A61B 2017/2845* (2013.01); *A61B 2017/2901* (2013.01); *A61B 2017/2902* (2013.01); *A61B 2017/292* (2013.01); *A61B 2017/2903* (2013.01); *A61B 2017/2908* (2013.01); *A61B 2017/2912* (2013.01); *A61B 2017/2916* (2013.01); *A61B 2017/2917* (2013.01); *A61B 2017/2919* (2013.01); *A61B 2017/2925* (2013.01); *A61B 2017/2926* (2013.01); *A61B 2017/2933* (2013.01); *A61B 2017/2936* (2013.01); *A61B 2017/2945* (2013.01); *A61B 2017/2946* (2013.01); *A61B 2017/2947* (2013.01); *A61B 2017/2948* (2013.01); *A61B 2017/320052* (2013.01); *A61B 2017/320095* (2017.08); *A61B 2018/0063* (2013.01); *A61B 2018/0091* (2013.01); *A61B 2018/00148* (2013.01); *A61B 2018/00196* (2013.01); *A61B 2018/00202* (2013.01); *A61B 2018/00309* (2013.01); *A61B 2018/00345* (2013.01); *A61B 2018/00601* (2013.01); *A61B 2018/00636* (2013.01); *A61B 2018/00916* (2013.01); *A61B 2018/00946* (2013.01); *A61B 2018/00952* (2013.01); *A61B 2018/1412* (2013.01); *A61B 2018/1455* (2013.01); *A61B 2018/1457* (2013.01); *A61B 2090/034* (2016.02)

(58) Field of Classification Search
CPC .... A61B 2017/2939; A61B 2017/2926; A61B 2017/2922; A61B 2017/294; A61B 2018/1452; A61B 2018/1455; A61B 2018/1457

See application file for complete search history.

(56) References Cited

U.S. PATENT DOCUMENTS

| | | |
|---|---|---|
| 8,968,311 B2 | 3/2015 | Allen, IV et al. |
| 8,968,313 B2 | 3/2015 | Larson |
| 9,737,357 B2 | 8/2017 | Dycus et al. |
| 9,861,378 B2 | 1/2018 | Allen, IV et al. |
| 9,956,030 B2 | 5/2018 | Allen, IV et al. |
| 11,406,408 B2 | 8/2022 | Holton et al. |
| 2013/0296848 A1* | 11/2013 | Allen, IV ............... A61B 17/29 606/41 |
| 2014/0025071 A1 | 1/2014 | Sims et al. |
| 2019/0175256 A1 | 6/2019 | Butler |
| 2019/0298399 A1 | 10/2019 | Boone et al. |
| 2020/0305908 A1 | 10/2020 | Holton et al. |

OTHER PUBLICATIONS

"U.S. Appl. No. 16/829,799, 312 Amendment filed Jun. 22, 2022", 7 pgs.
"U.S. Appl. No. 16/829,799, Advisory Action dated Feb. 18, 2022", 3 pgs.
"U.S. Appl. No. 16/829,799, Examiner Interview Summary dated Feb. 4, 2022", 2 pgs.
"U.S. Appl. No. 16/829,799, Final Office Action dated Dec. 6, 2021", 14 pgs.
"U.S. Appl. No. 16/829,799, Non Final Office Action dated Jun. 7, 2021", 16 pgs.
"U.S. Appl. No. 16/829,799, Notice of Allowance dated Mar. 23, 2022", 10 pgs.
"U.S. Appl. No. 16/829,799, PTO Response to Rule 312 Communication dated Jul. 12, 2022", 2 pgs.
"U.S. Appl. No. 16/829,799, Response filed Feb. 3, 2022 to Final Office Action dated Dec. 6, 2021", 15 pgs.
"U.S. Appl. No. 16/829,799, Response filed Mar. 7, 2022 to Advisory Action dated Feb. 18, 2022", 9 pgs.
"U.S. Appl. No. 16/829,799, Response filed Sep. 7, 2021 to Non Final Office Action dated Jun. 7, 2021", 16 pgs.
"U.S. Appl. No. 16/829,799, Supplemental Amendment and Response filed Mar. 10, 2022", 9 pgs.

* cited by examiner

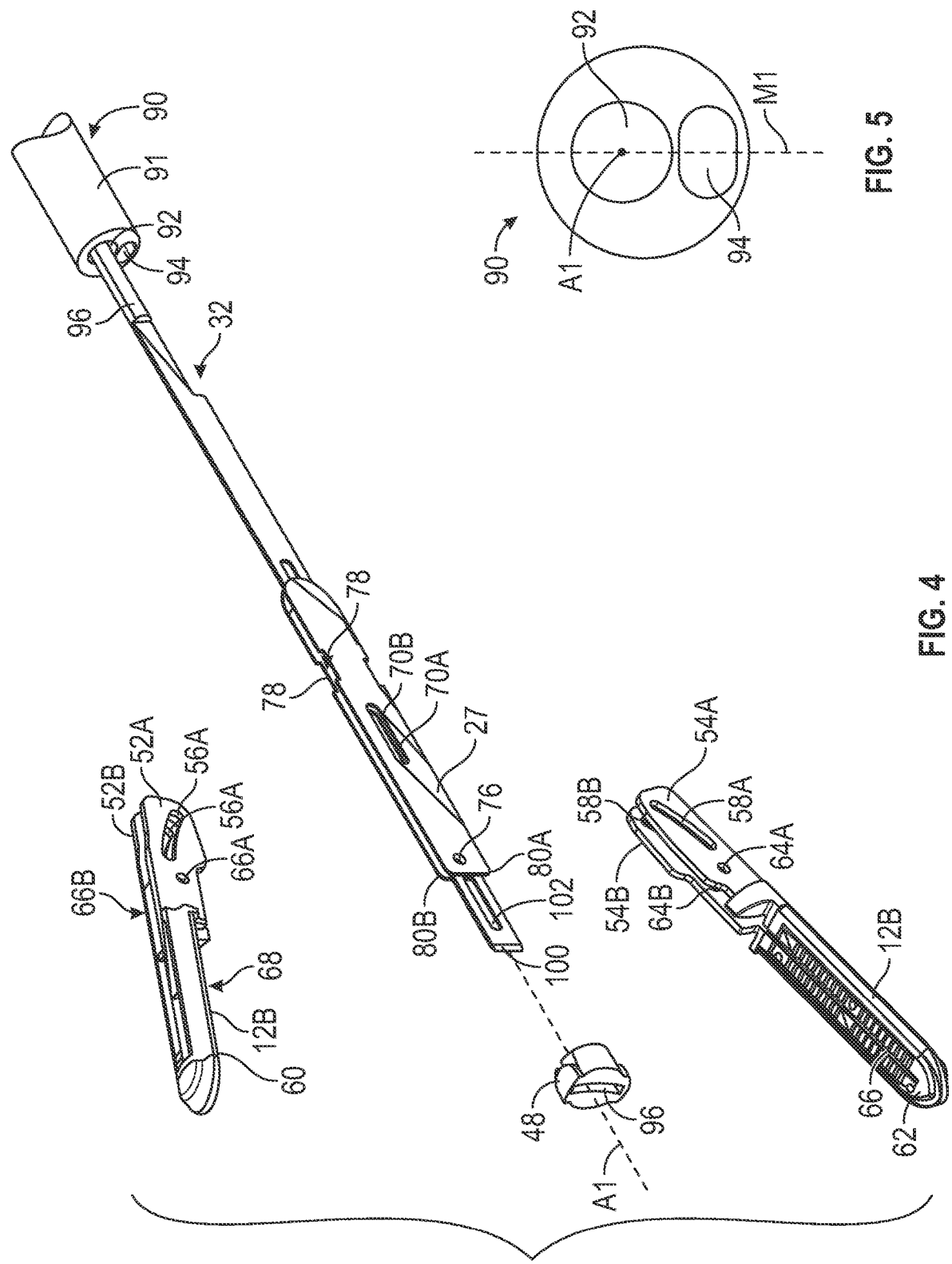

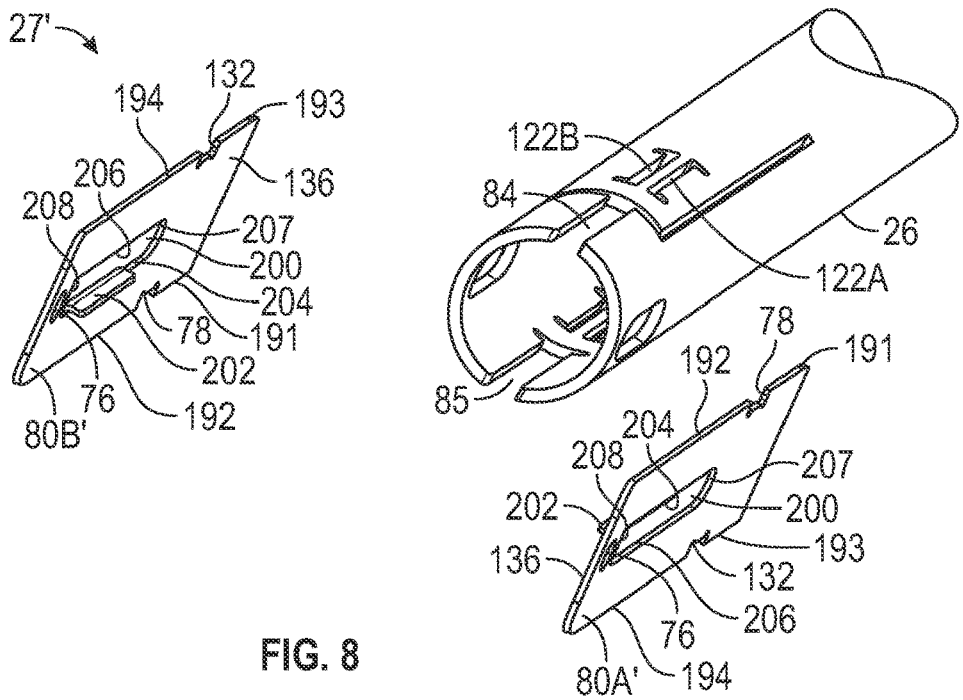
FIG. 8
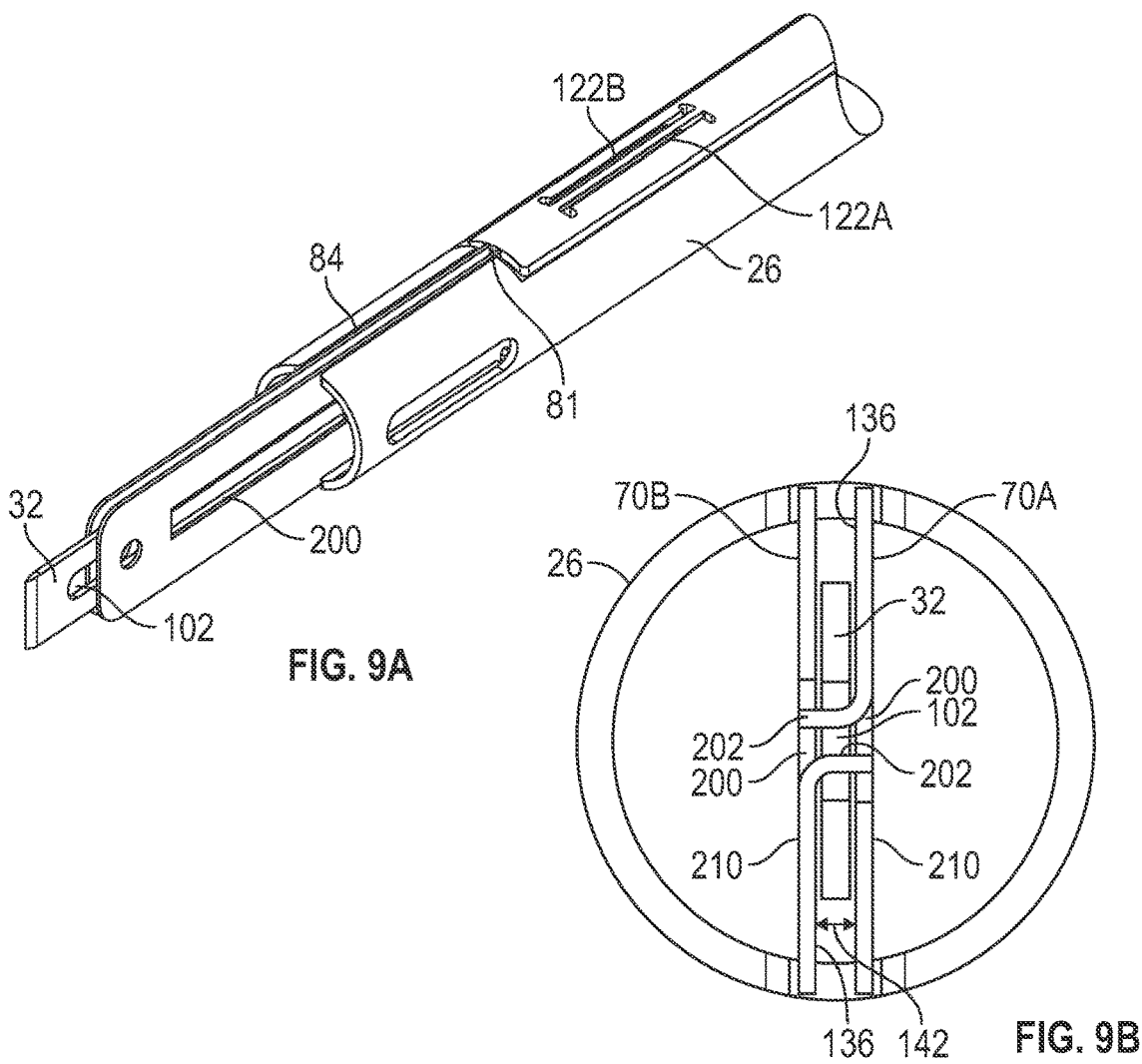
FIG. 9A
FIG. 9B

FORCEPS WITH TWO-PART DRIVE BAR

PRIORITY CLAIM

This application is a Continuation of U.S. patent application Ser. No. 16/829,799, filed Mar. 25, 2020, entitled "FORCEPS WITH TWO-PART DRIVE BAR", the disclosure of which is incorporated by reference in its entirety. This application also claims priority to U.S. Ser. No. 62/826,532, filed on Mar. 29, 2019, entitled "BLADE ASSEMBLY FOR FORCEPS", the disclosure of which is incorporated by reference in its entirety. This application also claims priority to U.S. Ser. No. 62/826,522 filed on Mar. 29, 2019, entitled "SLIDER ASSEMBLY FOR FORCEPS", the disclosure of which is incorporated by reference in its entirety. This application also claims priority to U.S. Ser. No. 62/841,476, filed on May 1, 2019, entitled "FORCEPS WITH CAMMING JAWS", the disclosure of which is incorporated by reference in its entirety. This application also claims priority to U.S. Ser. No. 62/994,220, filed on Mar. 24, 2020, entitled "FORCEPS DEVICES AND METHODS", the disclosure of which is incorporated by reference in its entirety.

TECHNICAL FIELD

This document pertains generally, but not by way of limitation, to surgical devices such as forceps, and more particularly, to a forceps device having an actuatable jaw that is configured to grasp, manipulate, and/or treat tissue.

BACKGROUND

This disclosure relates to surgical devices such as a forceps device. Forceps devices (hereinafter referred to simply as forceps), including but not limited to electrosurgical forceps, are often used for surgical procedures such as laparoscopic and open surgeries. The forceps can be used to manipulate, engage, grasp, or otherwise interact with anatomical features, such as a vessel or other tissue.

Forceps can include an end effector that is one or more of: rotatable, openable, closeable, extendable, retractable and capable of supplying an input such as electrosurgical energy or ultrasound. For example, jaws located at a distal end of the forceps can be actuated via elements at a handpiece of the forceps to cause the jaws to open and close and thereby engage a vessel or other tissue. Forceps may also include an extendable and retractable blade, or other end effector type device.

Overview

Illustrative forceps having actuatable jaws facilitated by one or more of flanges with cam slots or tracks and a drive bar formed from a pair of drive bar struts is disclosed herein. The drive bar can receive the drive pin (camming or cam pin) and translate the drive pin along the cam slots to transition the forceps between a closed position and an open position. The present inventors have recognized that drive bars can be improved to simplify the design and manufacturing of the forceps, reduce the cost, and maximize the available space for other components. In an example, the drive bar can include a pair of drive bar struts that are, in one example, formed from two substantially identical plates. The two plates can separately couple to an inner shaft, e.g., via snapping into slots provided in the inner shaft. Being able to use two plate that are substantially identical and not having to preassemble drive bar parts prior to coupling the drive bar to the inner shaft can simplify the design and manufacturing of the forceps, reduce the cost, and maximize the available space for other components.

In an example surgical forceps can comprise a drive pin, an outer shaft defining a longitudinal axis, a first jaw pivotably connected to the outer tube, the first jaw including a first set of flanges located at a proximal portion of the first jaw, each flange of the first set of flanges including a first track for receiving the drive pin, a second jaw pivotably connected to the outer tube, the second jaw including a second set of flanges located at a proximal portion of the second jaw, each flange of the second set of flanges including a second track for receiving the drive pin; an inner shaft located within the outer shaft and extending along the longitudinal axis, and a drive bar coupled to and extending distally from the inner shaft. The drive bar including a pair of drive bar struts extending from a distal portion of the inner shaft and positioned laterally inward of the first and second set of flanges, the drive pin securable to the pair of drive bar struts, wherein the drive bar is translatable within the outer shaft to drive the drive pin along the first set of tracks and the second set of tracks to move the first jaw and the second jaw between open and closed positions.

In another example, a surgical forceps can comprise a drive pin, an outer shaft extending along a longitudinal axis, a first jaw and a second jaw each pivotable with respect to the outer shaft, the first jaw including a first set of flanges, each first flange including a first track receiving the drive pin therein, and the second jaw including a second set of flanges, each second flange including a second track receiving the drive pin therein, and an inner shaft located within the outer shaft and extending along the longitudinal axis, a drive bar coupled to and extending distally from the inner shaft. The drive bar includes a first drive bar strut extending from and separately coupled to the inner shaft and a second drive bar strut extending from and separately coupled to the inner shaft, the drive pin connected to the first and second drive bar, the drive bar translatable within the outer shaft to translate the drive pin along the first set of tracks and the second set of tracks to move the first jaw and the second jaw between open and closed positions.

In another example, a surgical forceps comprise a drive pin, an outer shaft defining a longitudinal axis, a first jaw pivotably connected to the outer tube, the first jaw including a first set of flanges located at a proximal portion of the first jaw, each flange of the first set of flanges including a first track for receiving the drive pin. The forceps can include a second jaw connected to the outer tube, an inner shaft located within the outer shaft and extending along the longitudinal axis, a drive bar coupled to and extending distally from the inner shaft. The drive bar including: a pair of drive bar struts extending from a distal portion of the inner shaft, the drive pin securable to the pair of drive bar struts, wherein the drive bar is translatable within the outer shaft to drive the drive pin along the first set of tracks to move the first jaw relative to the second jaw between open and closed positions, and a blade located within the inner shaft and the drive bar, the blade translatable to extend between the first jaw and the second jaw, wherein each of the drive bar struts include a projection extending from a first edge of the drive bar struts forming an L-shaped plate, and wherein a first edge, a second edge, a first face, and a second face of the blade do not contact the drive bar.

The features described herein can be used with other devices besides forceps, such as medical devices (e.g., instruments) for performing treatment, diagnosis and imaging. The devices and methods can be employed in a variety of medical areas, including, but not limited to, general surgery, gynecology, urology, respiratory, cardiovascular, or any other suitable area.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

FIG. 4 is an expanded view of a portion of the forceps, according to an example of the present application.

FIG. 5 is a front end view of a distal plug of the forceps, according to an example of the present application.

FIG. 8 is an expanded view of a drive bar and an inner shaft, according to another example of the present application.

FIG. 9A is a perspective view of the drive bar and the inner shaft shown in FIG. 8 including the blade.

FIG. 9B is a cross-sectional view of the drive bar, the inner shaft, and the blade, according to an example of the present application.

DETAILED DESCRIPTION

A medical device including a handpiece that operates an end effector allows a surgeon to control the end effector of the device to actuate one or more functions of the end effector. Actuation of the end effector can be facilitated by one or more actuation systems of the handpiece that can retract, extend or rotate one or more shafts to control the actions of the end effector.

This disclosure is generally related to medical devices, such as surgical instruments. Although the present application is described with reference to a forceps, other end effectors can be used with and operated by the handpiece described herein. In addition, other handpieces can be connected to and can control the end effectors described herein. This disclosure includes examples of handpieces including one or more actuation systems, examples of end effectors, and examples where the disclosed actuation systems and end effectors can be used together in a medical device.

The forceps can include a medical forceps, a cutting forceps, an electrosurgical forceps, or any other type of forceps. The forceps can include an end effector that is controlled by a handpiece including an actuation system to be one or more of: rotatable, openable, closeable, extendable, and capable of supplying electrosurgical energy or ultrasound. For example, jaws located at a distal end of the forceps can be actuated via one or more actuators at a handpiece of the forceps to cause the jaws to open, close and rotate to engage a vessel or other tissue. Forceps may also include an extendable and retractable blade, such as blades that can be extended distally in between a pair of jaws to separate a first tissue from a second tissue.

In this disclosure, relative terms, such as, for example, "about", "generally", or "substantially" are used to indicate a possible variation of ±10% in a stated numeric value or within ±10° of the numeric value.

Figure 1A:
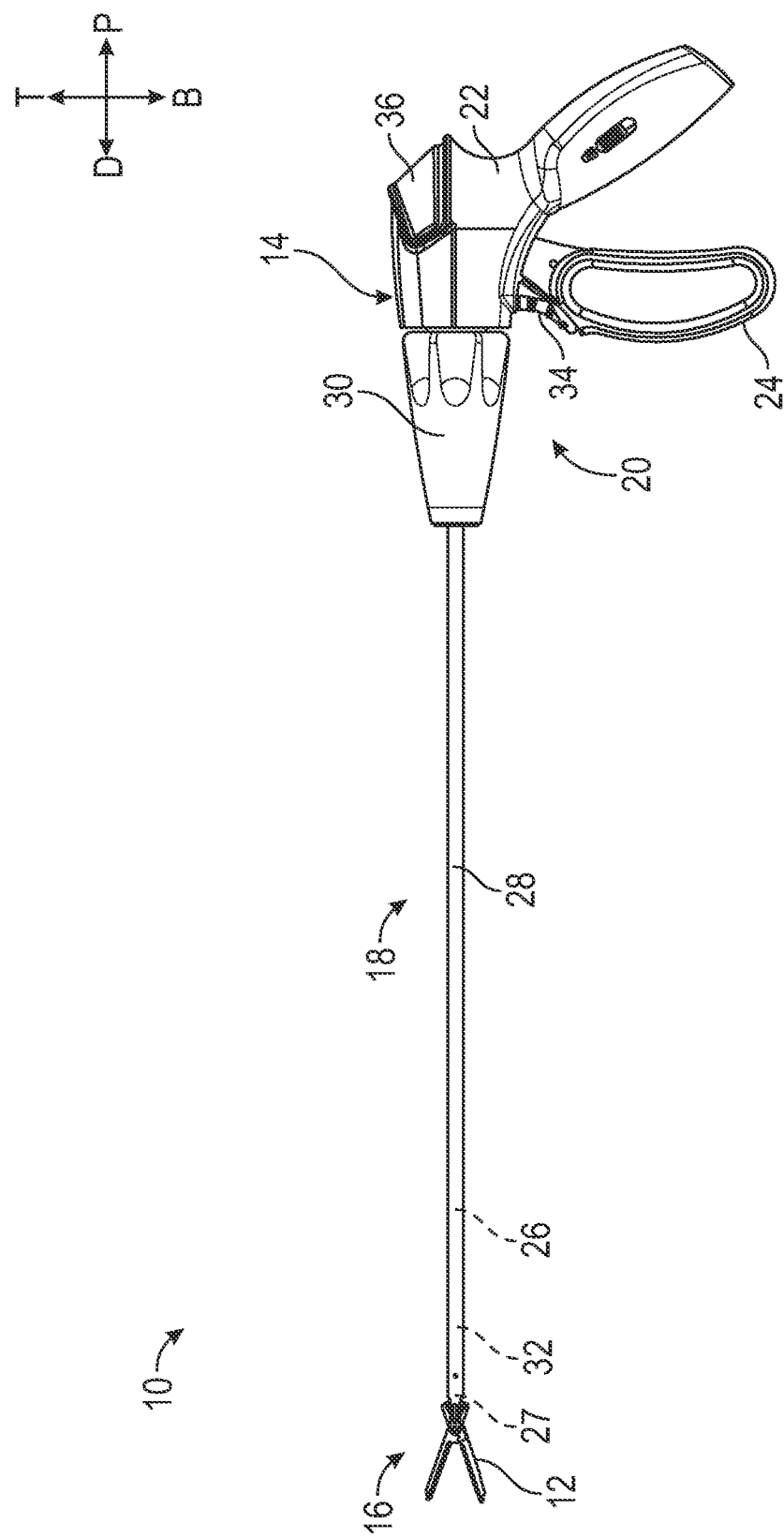
FIG. 1A is a side view of a forceps having jaws in an open configuration, according to an example of the present application.
Figure 1B:
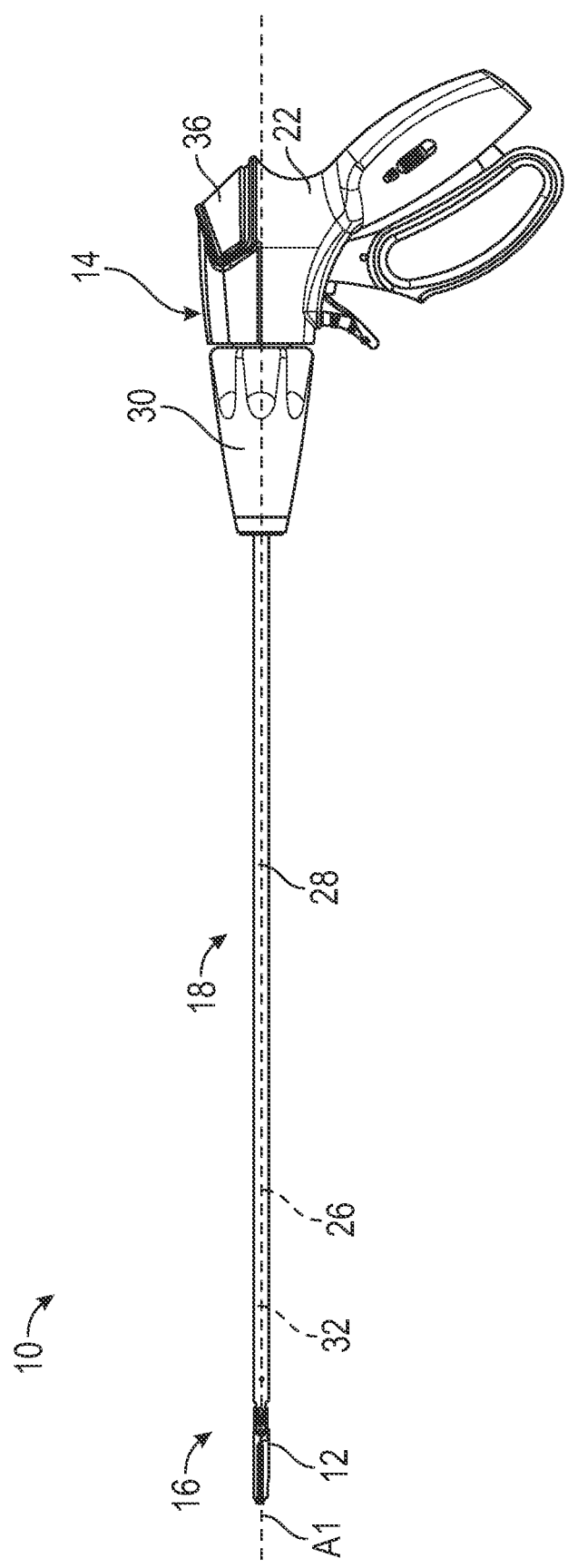
FIG. 1B is a side view of the forceps in FIG. 1A having the jaws in a closed configuration.

FIG. 1A illustrates a side view of a forceps 10 with jaws 12 in an open position and FIG. 1B illustrates a side view of the forceps 10 with jaws 12 in a closed position. Directional descriptors such as proximal and distal are used within their ordinary meaning in the art. The proximal direction P and distal direction D, as well as top T and bottom B, are indicated on the axes provided in FIG. 1A. The forceps can include a handpiece 14, one or more actuators 20, an outer shaft 28 (or outer tube), an inner shaft 26 (or inner tube), a drive bar 27, and an end effector 16.

The forceps 10 can include the handpiece 14 at a proximal end and the end effector 16 at a distal end. An intermediate portion 18 can extend between the handpiece 14 and the end effector 16 to operably couple the handpiece 14 to the end effector 16. Various movements of the end effector 16 can be controlled by one or more actuation systems 20 of the handpiece 14. In the illustrative example, the end effector 16 can include the jaws 12 that are capable of moving between an open position and a closed position. The end effector 16 can be rotated along a longitudinal axis A1 of the forceps 10. The end effector 16 can include a cutting blade and an electrode for applying electrosurgical energy.

The forceps 10 can include the jaws 12, a housing 22, a lever 24, the inner shaft 26, the drive bar 27, the outer shaft 28, a rotational actuator 30, a blade assembly 32, a trigger 34 and/or an activation button 36. In this example, the end effector 16, or a portion of the end effector 16 can be one or more of: opened, closed, rotated, extended, retracted, and electrosurgically energized.

To operate the end effector 16, the user can displace the lever 24 proximally to drive the jaws 12 from the open position (FIG. 1A) to the closed position (FIG. 1B). In the example of forceps 10, moving the jaws 12 from the open position to the closed position allows a user to clamp down on and compress a tissue. The handpiece 14 can also allow a user to rotate the end effector 16. For example, rotating rotational actuator 30 causes the end effector 16 to rotate by rotating both the inner shaft 26, drive bar 27, and the outer shaft 28 together.

In some examples, with the tissue compressed, a user can depress the activation button 36 to cause an electrosurgical energy to be delivered to the end effector 16, such as to an electrode. Application of electrosurgical energy can be used to treat the tissue such as seal or otherwise affect the tissue being clamped. In some examples, the electrosurgical energy can cause tissue to be sealed, ablated, and/or coagulated. Example electrodes are described herein, but electrosurgical energy can be applied to any suitable electrode.

In some examples, the forceps 10 can be used to cut the treated tissue via the blade assembly 32 (also referred to as blade 32). For example, the handpiece 14 can enable a user to extend and retract the blade 32. The blade 32 can be extended by displacing the trigger 34 proximally. The blade 32 can be retracted by allowing the trigger 34 to return distally to a default position. The default position of the trigger 34 is shown in FIG. 1. In some examples, the handpiece 14 can include features that inhibit the blade 32 from being extended until the jaws 12 are at least partially closed, or fully closed.

The forceps 10 can be used to perform a treatment on a patient, such as a surgical procedure. In an example, a distal portion of the forceps 10, including the jaws 12, can be inserted into a body of a patient, such as through an incision or another anatomical feature of the patient's body. While a proximal portion of the forceps 10, including the housing 22 remains outside the incision or another anatomical feature of the body. Actuation of the lever 24 causes the jaws 12 to clamp onto a tissue. The rotational actuator 30 can be rotated via a user input to rotate the jaws 12 for maneuvering the jaws 12 at any time during the procedure. Activation button 36 can be actuated to provide electrical energy to jaws 12 to cauterize, desiccate, or seal the tissue within the closed jaws 12. Trigger 34 can be moved to translate the blade 32 distally in order to cut the tissue within the jaws 12.

Figure 2:
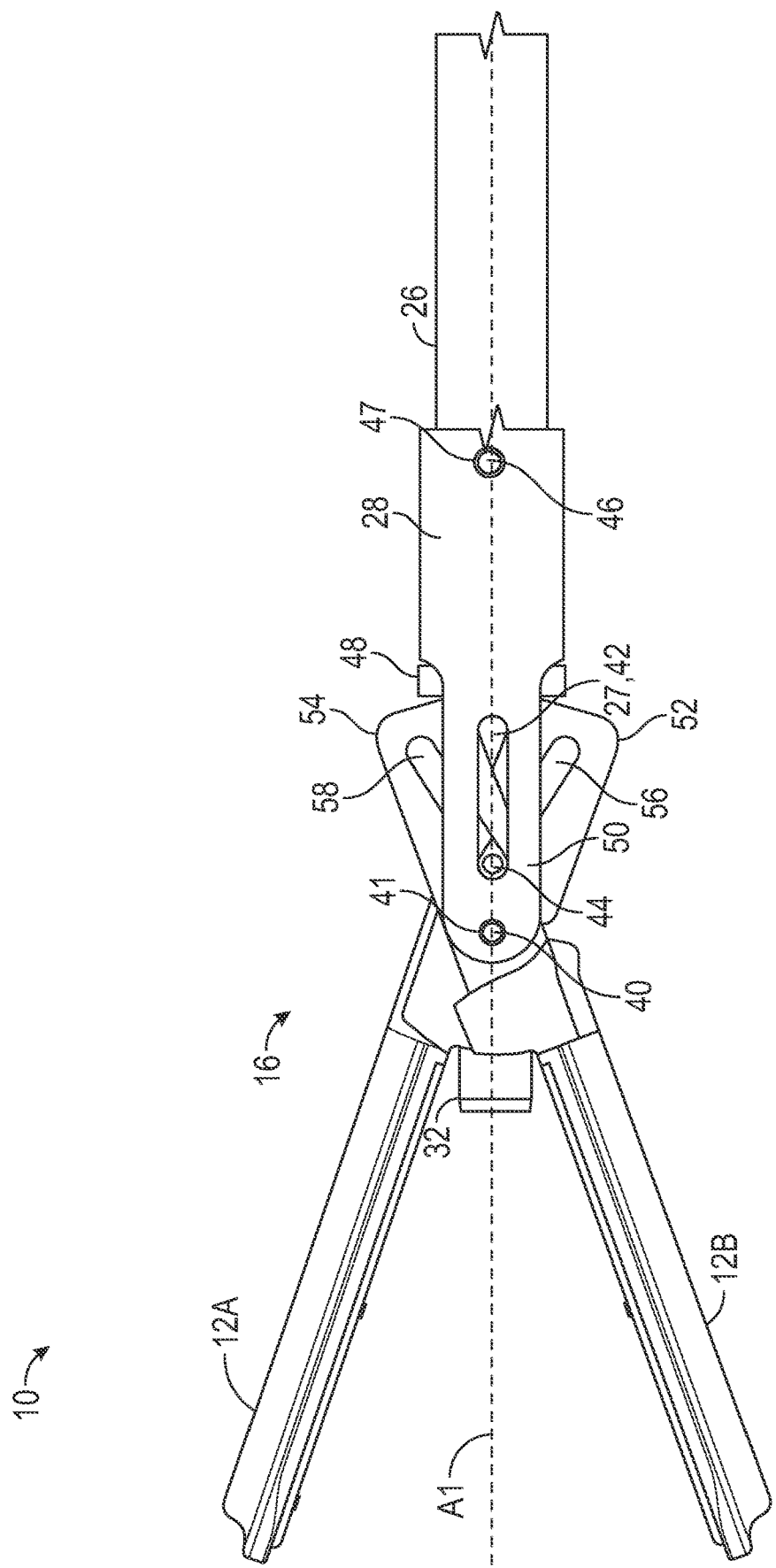
FIG. 2 is a side view of a portion of the forceps, according to an example of the present application.

FIG. 2 illustrates a side view of a portion of the forceps 10 in an open position. The end effector 16 can be configured as articulating jaws 12A (top jaw 12A) and 12B (bottom jaw 12B) (collectively referred to as jaws 12) configured to manipulate, engage, grasp, or otherwise interact with anatomical features, such as a vessel or other tissue. In one example, the jaws 12 are double acting jaws, where both the top jaw 12A and the bottom jaw 12B can move (rotate) relative to the outer tube 28. In one example, only one of the top jaw 12 and the bottom jaw 12B rotates relative to the outer tube 28. That is, in one example, the top jaw 12 can be configured to rotate relative to the bottom jaw 12B and the outer tube 28. In another example, the bottom jaw 12 can be configured to rotate relative to the top jaw 12A and the outer tube 28.

The forceps 10 can include the top jaw 12A, the bottom jaw 12B, a guide 46 (or proximal pin), a drive pin 44 (or cam pin 44), and a pivot pin 40. The jaws 12 of the end effector 16 can be connected to the outer shaft 28 via the pivot pin 40. The pivot pin 40 can extend through a portion of the jaws 12 such that the pivot pin 40 can be received by outer arms 50 of the outer shaft 28 (only one outer arm 50 visible in FIG. 2).

The forceps 10 can have a reciprocating drive bar 27 coupled to the inner shaft 26 at least partially positioned within the outer shaft 28. As discussed herein, the drive bar 27 can be coupled to and extend distally from the inner shaft 16. The drive bar 27 can have the drive pin 44 (or cam pin 44) attached thereto (for example at a distal end thereof). Thus, the drive bar 27 and the drive pin 44 thereby, can be moveable relative to the outer shaft 28 in a translatable manner. Movement of the drive bar 27 (visible through slot 42 in the arm 50 of the outer shaft 28) can traverse the drive pin 44 along a longitudinal axis A1 of the outer shaft 28 and a longitudinal axis of the jaws 12 and can move the jaws 12 as a result of a camming action as further discussed below.

The guide 46 can be secured to the outer shaft 28 such as by insertion into bores 47A and 47B (collectively referred to as bores 47; only one bore 47 is visible in FIG. 2). In some examples, the bores 47 can be substantially coaxial and can be substantially perpendicular to the longitudinal axis A1. In such cases, the guide 46 can be positioned in the bores 47 and can be on the axis defined by the bores 47, substantially perpendicular to the axis A1. The bores 47 can also be substantially centered about the outer shaft 28 to center the guide 47. In some examples, the bores 47 can be offset from the axis A1 (either above, below) and substantially perpendicular to the axis A1. In other examples, the bores 47 can cross a lateral plane defined in part by the axis A1 such that one bore is above the axis A1 and one is below; the axis defined by the bores 47 can run through the axis A1 or can be offset therefrom in such a configuration. The axial tracks 70, 72 of the drive bar 27 and the inner shaft 26 (see FIG. 3) can be configured to match the orientation of the guide 46 to allow the drive bar 27 and the inner shaft 26 to translate with respect to the guide 46.

The outer shaft 28 can include a pair of outer arms 50. The forceps 10 can further include a distal plug 48 that can be a plug positionable within the outer shaft 28 between the outer arms 50 such that the drive bar 27 and blade 32 can translate through the distal plug 48. As discussed herein, the distal plug 48 can include a channel extending therethrough to allow the drive bar 27 and blade 32 to extend through (and translate with respect to) the distal plug 48. The distal plug 48 is discussed in further detail below.

As shown in FIG. 2, each of the jaws 12A and 12B may have a pair of spaced flanges 52, 54, respectively (only two, one for each of the jaws 12A and 12B are visible in FIG. 2). The arrangement and construction of the flanges 52, 54 will be described in further detail subsequently. According to some examples, the pair of flanges 52, 54 for the jaws 12 can be arranged generally parallel with one another (e.g., having interfacing generally parallel spaced inner surfaces) along a longitudinal direction but spaced by the inner drive bar 27. At least one of the pair of flanges 52, 54 can be pivotably coupled to the outer shaft 28 via the pivot pin 40.

Each of the flanges 52, 54 can also have tracks 56, 58, respectively (sometimes referred to as a cam slot or slot herein) spaced from the pivot pin 40. The tracks 56, 58 can be configured to receive the drive pin 44, which can be moveably secured therein. The drive pin 44 can have a diameter less than a width of the tracks 56, 58 so as to be moveably received by the tracks 56, 58. As the drive bar 27 moves, for example, by applying linear motion to the inner shaft 26, the drive pin 44 can traverse along a longitudinal length of the tracks 56, 58. The drive pin 44, drive bar 27, and inner shaft 26 (coupled to part of one or more actuators 20) can be configured for reciprocating movement relative to the outer shaft 28 such that the drive pin 44 can traverse the tracks 56, 58 in a reciprocating manner. Each track 56, 58 can be configured to work as a cam so that as the drive pin 44 traverses the longitudinal length of the tracks 56, 58 the jaws are driven from a first open position (shown in FIG. 1A) towards and to a second closed (grasping) position (FIG. 1B) or vice versa. The shape and size of the flanges 52, 54 including the shape, size and arrangement of the tracks 56, 58 can be configured to limit or control the degree of contact that other portions of the jaws 12 can have with the vessel or other tissue being treated.

The tracks 56, 58 for each of the pair of flanges 52, 54 can be aligned with one another and can have generally a same shape. Put another way, the tracks 56, 58 of each of the pair of flanges 52, 54 can be aligned when viewing the end effector 16 from the side as illustrated in FIGS. 1A, 1B, and 2. Thus, the tracks 56, 58 of each of the jaws 12 can be aligned in a direction perpendicular to a direction of a longitudinal axis A1 of the jaws 12. The pivot pin 40 can be secured to the outer shaft 28. Pivot bores on the flanges 52, 54 can be secured to the pivot pin 40. The drive pin 44 can be fitted into the tracks 56, 58 on each of the pair of flanges 52, 54. As shown particularly in FIG. 2, the pins 40, 44, and 46 can be arranged parallel with one another and along the longitudinal axis A1, the tracks 54 can be the same size, and can be aligned as discussed above an illustrated.

Figure 3:
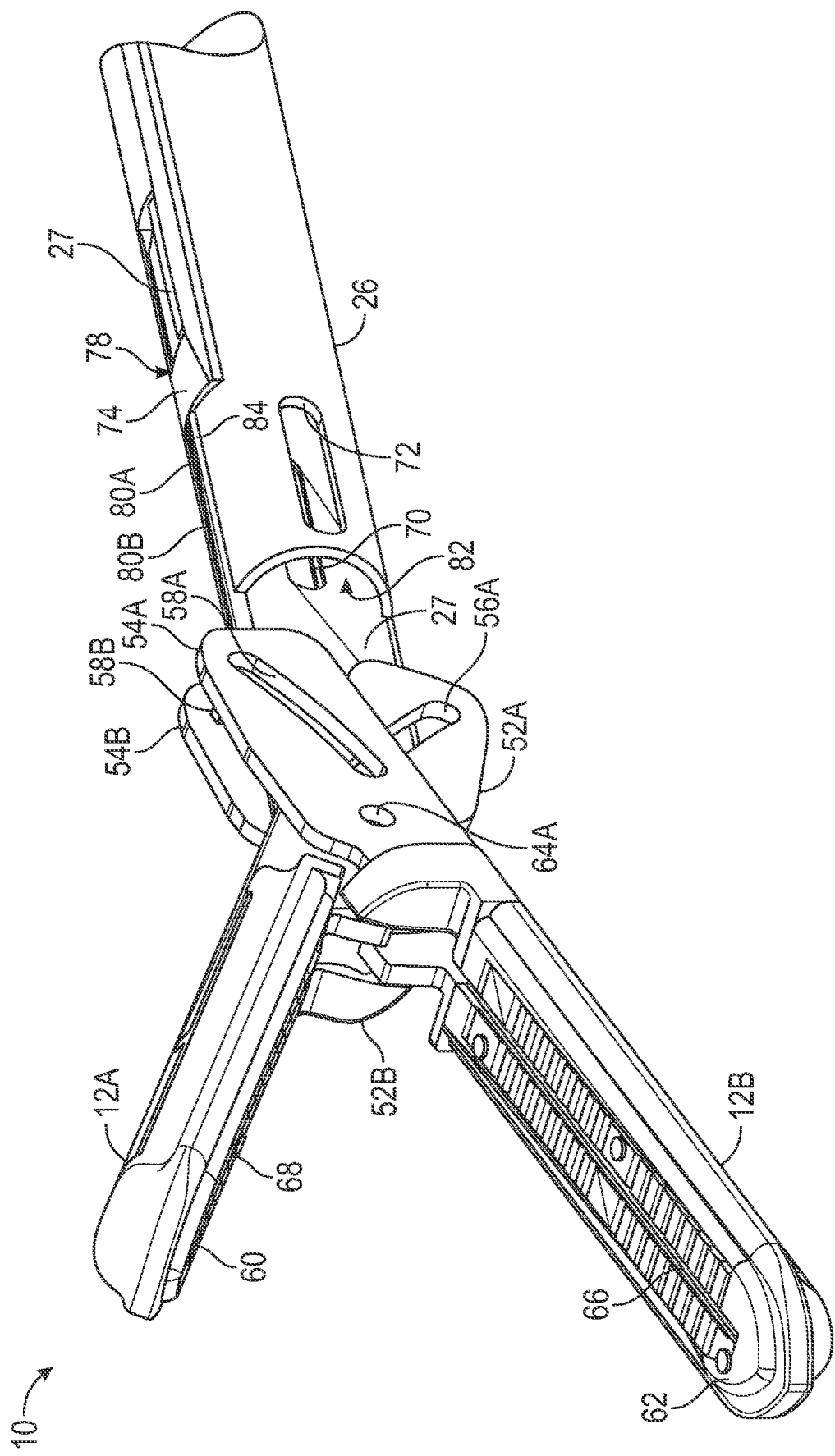
FIG. 3 is a perspective view of a portion of the forceps, according to an example of the present application.

FIG. 3 illustrates a perspective view of a portion of the forceps 10. The top jaw 12A can include flanges 52A, 52B (collectively flanges 52) and an upper grip plate 60, and the lower jaw 12B can include flanges 54A, 52B (collectively referred to as the flanges 52) and a lower grip plate 62. The flanges 52A and 52B can include tracks 56A and 56B, respectively (collectively referred to as tracks 56; track 56B shown in FIG. 4). The flanges 54A and 54B can include tracks 58A and 58B, respectively (collectively referred to as tracks 58).

The jaws 12 can be rigid members configured to engage tissue. The jaws 12 can be coupled to the outer shaft 28, such as pivotably coupled, via the pivot pin 40 (see FIG. 2). The pivot pin 40 can extend through a portion of the jaws 12 such as a pivot bore of each of the jaws 12 such that the pivot pin 40 can be received by the outer arms 50 (see FIG. 1) of the outer shaft 28. For examples, flanges 52A and 52B can each have pivot bores 64A and 64B, respectively, and flanges 54A and 54B can have pivot bores 66A and 66B (see FIG. 4).

As seen in FIG. 3, flanges 52 can be interlaced with flanges 54. In other examples, the flanges 54 can be positioned laterally outward of flanges 52 or alternatively, flanges 52 can be positioned laterally outward of flanges 54.

The grip plates 60, 62 of the jaws 12 can each be a rigid or semi-rigid member configured to engage tissue and/or the opposing jaw to grasp tissue, such as during electrosurgical procedure. One or more of the grip plates 60, 62 can include one or more of serrations, projections, ridges, or the like configured to increase engagement pressure and friction between the grip plates 60, 62 and tissue. The flanges 52 of the upper jaw 12A can extend proximally away from the grip plate 60. Similarly, the flanges 54 of the lower jaw 12B can extend proximally away from the grip plate 62. The jaws 12 can each include an electrode configured to deliver electricity to tissue (optionally through the grip plates 60, 62), a frame supporting the electrode, and blade slots 66, 68 configured to receive a blade between the jaws 12, as discussed herein.

The tracks 56 of the jaw 12A and the tracks 58 of the flanges 12B can each be a slot, channel, path, or track in the flanges 52 and 54, respectively. In some examples, the tracks 56 and 58 can be located proximally of the pivot pin 40 when the pivot pin 40 is coupled to the jaws 12 (and optionally to the outer shaft 28). The tracks 56 and 58 can be shaped to receive the drive pin 44 therein. In some examples, the tracks 56 and 58 can be slots or channels configured to receive the drive pin 44 therethrough to connect the drive bar 27 to the flanges 52 and 54 (and therefore to the jaws 12).

The tracks 56 and 58 can be straight in some examples and can be arcuately shaped in some examples. In any example, the tracks 56 and 58 can be configured to allow the drive pin 44 to travel along the tracks 56 and 58 simultaneously to open and close the jaws 12.

It is understood that various modifications can be made to the surgical forceps described herein. For example, the jaws may not be dual acting according to some examples but can rather be single acting. A single flange can be utilized rather than a pair of flanges in some examples. Although the jaws are described as having a flange (or flanges), in some cases the jaws may not utilize a flange such that features such as the track can be directly through a body portion of the jaw itself, for example.

As seen in FIG. 3, the drive bar 27 extends distally from the inner shaft 26. The drive bar 27 and the inner shaft 26 both include axial tracks 70, 72, respectively, for receiving the guide 46 (see FIG. 2). For example, the drive bar 27 can include a pair of axial tracks 70A and 70B (see FIG. 4, collectively referred to as axial tracks 70) and the inner shaft 26 include pair of axial tracks 72A and 72B (collectively referred to as axial tracks 72). The axial tracks 70, 72 can also be referred to as axial slots or channels. Additionally, axial tracks 70 of the drive bar 27 can be referred to as proximal slots of the drive bar 27 and axial tracks 72 of the inner shaft 26 can be referred to as distal slots of the inner shaft 26, discussed more herein. The axial tracks 70 can each be axial slots extending laterally through walls of the drive bar 27 such that the guide 50 extends through the drive bar 27. The axial tracks 72 can be channels, grooves, recesses, or other guides configured to receive the guide 46.

The drive bar 27 can be coupled to the inner shaft 26. In an example, the drive bar 27 can include a pair of drive bar struts 80A and 80B (collectively referred to as drive bar struts 80). As discussed more herein, the drive bar struts 80 and the inner shaft 26 can include corresponding features such as projections, tabs, grooves, recesses, etc., to couple the drive bar struts 80 to the inner shaft 26. Once coupled, the drive bar struts 80 are axially and rotationally coupled to the inner shaft 26. In an example, the inner shaft 26 can include one or more slots (e.g., slot 84) and one or more flexible tabs 74 to enable insertion of the drive bar struts 80 into the inner shaft 26. For example, as the drive bar struts 80 are inserted into the opening 82 and along the slot 84 of the inner shaft 26, the flexible tab 74 can flex to allow a portion of the drive bar struts 80 to pass and return to an original position while being positioned within the corresponding recesses 78 in the drive bar struts.

As discussed herein, the drive bar 27 can receive the drive pin 44, e.g., within the drive pin openings 76, at a distal end of the drive bar struts 80. Therefore, the drive bar 27 and the drive pin 44 thereby, can be moveable relative to the outer shaft 28 and to the first jaw 12A and/or the second jaw 12B in a translatable manner.

FIG. 4 illustrates an expanded view of a portion of the forceps 10. The distal plug 48 can be a plug positionable within the outer shaft 28 (see FIG. 2). The distal plug 48 can include a blade channel 92 extending therethrough to allow the blade 32 to extend through (and translate with respect to) the distal plug 48. In an example, the blade channel 96 is centrally located along the longitudinal axis A1.

The blade 32 can be an elongate cutting member including one or more sharpened edges 100 configured to cut or resect tissue or other items. The blade 32 can be coupled to a blade shaft 96. The blade 32 can be located within the outer shaft 28 (and within the inner shaft 26 and the drive bar 27) and can extend along the axis A1. The blade 32 can be translatable with respect to the inner shaft 26, the drive bar 27, and the outer shaft 28 to extend between (or into) the top jaw 12A and the bottom jaw 12B. As discussed herein, the blade 32 can extend axially through the drive bar 27 and through the flanges 52, 54 such that the blade 32 is in a position laterally inward of the first set of flanges 52, the second set of flanges 54, and the pair of drive bar struts 80.

The forceps 10 can include a guide tube 90 that can be positioned within the inner shaft 26 and the outer shaft 28 and can extend through the outer shaft 28 and the inner shaft 26. The guide tube 90 that can include a body 91 defining a blade bore 92 and a wire routing bore 94. The body 91 can extend along the axis A1 and can be substantially cylindrical in some examples, but can have other shapes in other examples, such as an oval prism, a rectangular prism, a hexagonal prism, an octagonal prism, or the like. The body 91 can be configured, such as sized and shaped, to be complimentary to an internal bore of the inner shaft 26. The blade bore 92 and the wire routing bore 94 can each be bores extending axially through the body 91 along the axis A1. The blade bore 92 can be sized and shaped to receive the shaft 96 of the blade 32 therethrough and can be configured to allow for translation of the shaft 96 within the guide tube 90 to allow the blade 32 to be operated from the handle such that the blade 32 can translate within the blade channels of the jaws 12.

In operation of some examples, the blade 32 can be translated distally between the drive bar 27 into tracks of the jaws 12 when the jaws are between the open position and the closed position or when the jaws 12 are in the closed position. The blade 32 can be used to cut tissue or other items between the jaws 12.

FIG. 4 illustrates the blade 32 including a blade track 102 (or blade channel 102). The blade track 102 can be configured to contact the guide 46 to limit axial translation of the blade 32 with respect to the guide 46 and the outer shaft 28. For example, the proximal edge (which can be rounded complimentary to the guide 46) can be configured to contact the guide 46 to limit distal translation of the blade 32 with respect to the inner shaft 26, the drive bar 27, the outer shaft 28, and the jaws 12. Also, contact between one or more of the guide 46, the drive pin 44, and the pivot pin 40 with the top edge of the blade track 102 can help limit downward and/or upward movement of the blade 32 with respect to the inner shaft 26, the drive bar 27, the outer shaft 28, and the jaws 12. Such contact can also help limit rotation of the blade 32, such as about the axis A1.

FIG. 5 illustrates a front view of the guide tube 90. In an example, the blade bore 92 and the wire routing bore 94 are positioned along longitudinal axis A1 and the midline M1 of the guide tube 90. In one example, the wire routing bore 94 can be offset from the midline M1 of the guide tube 90.

FIGS. 6A-15 illustrate different examples of the drive bars having drive bar struts coupled to an inner shaft. FIGS. 6A-7B illustrate the example shown in the previous figures. The drive bar 27 can be coupled to the inner shaft 26. In an example, the drive bar 27 can be formed from a pair of drive bar struts 80A, 80B (collectively drive bar struts 80) extending from a distal portion of the inner shaft 26. In an example, the drive bar struts 80 are substantially identical plates. For example, the drive bar struts 80 can have the same shape, length, and features. That is, features such as projections, grooves, recesses, axial tracks and bores are in substantially the same location and have the same size between the two plates. By having two identical plates for the drive bar struts 80 of the drive bar 27, manufacturing of the drive bar struts 27 can be simplified, the overall production cost can be reduced, and assembly of the forceps can be made easier. In another example, the drive bar struts 80A and 80B can be different from each.

The drive bar struts 80A and 80B can extend from a proximal end 110 to a distal end 112. As discussed herein, the drive bar struts 80 can include the axial tracks 71 and the bores 76. In an example, the bores 76 are distal to the axial tracks 71. The drive bar struts 80 can include a first edge 114, a second edge 116 opposite the first edge 114, and a blade facing surface 136 extending between the first and second edges 114, 116. The blade facing surfaces 136 can be a face of the drive bar struts 80 that are positioned adjacent to each other such that they form a channel (e.g., a blade channel) that is configured to receive a blade, as discussed herein. The first edge 114 and the second edge 116 can be configured to have a shape (profile) that corresponds to features on the inner shaft 26 such that the drive bar struts 80 can couple to the inner shaft 26. In an example, the drive bar struts 80 can have a recess 78, along the first edge 114, toward the proximal end 110 and have a recess 132, along the second edge 116, toward the proximal end 110. The first edge 114 includes a proximal portion 191 (proximal to recess 78) and a distal portion 192 (distal to recess 78). Similarly, the second edge 116 includes a proximal portion 193 (proximal to recess 132) and a distal portion 194 (distal to recess 132).

Figure 7A:
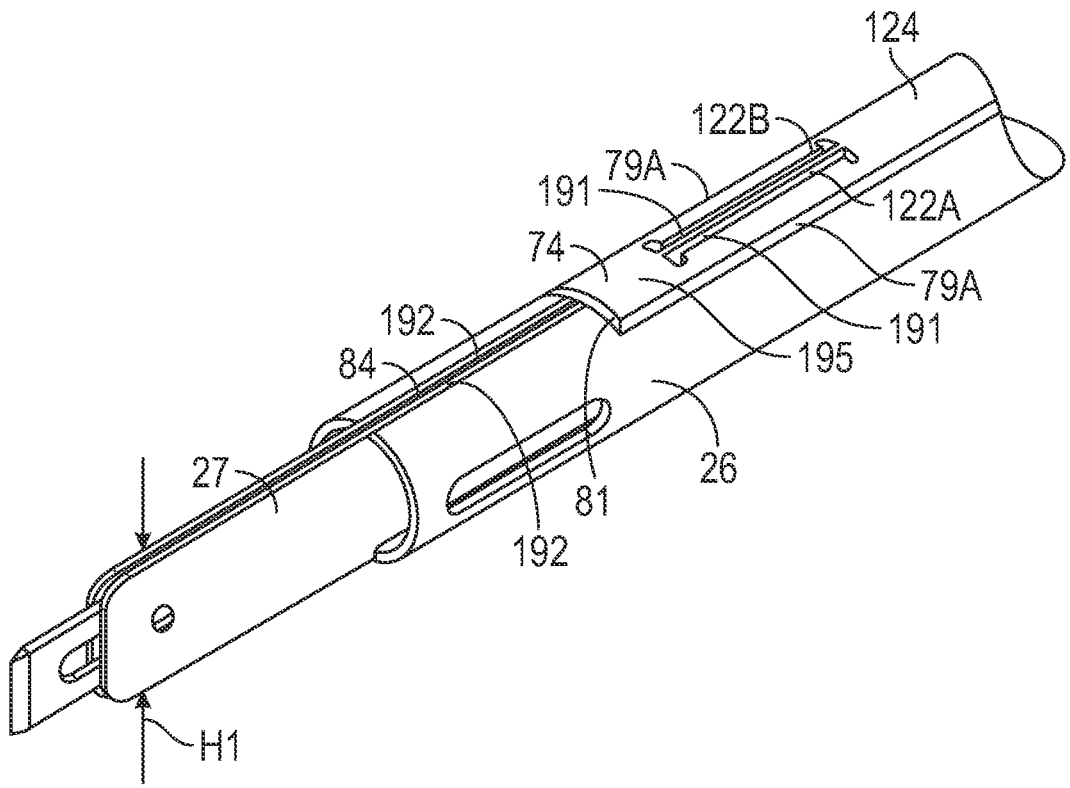
FIG. 7A is a perspective view of the drive bar and the inner shaft shown in FIGS. 6A and 6B including the blade, according to an example of the present application.
Figure 7B:
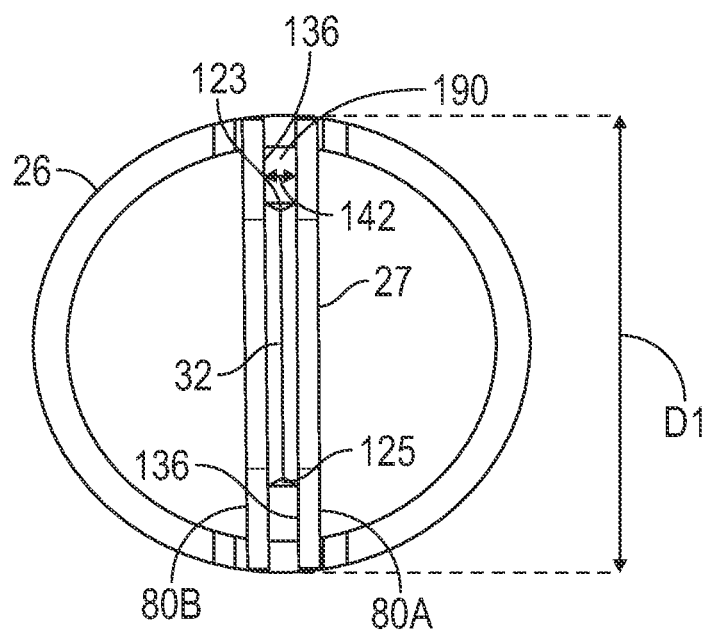
FIG. 7B is a cross-sectional view of the drive bar and the inner shaft shown in FIG. 7A.

As seen in FIG. 7B, an outer diameter D1 of the inner shaft 26 is substantially equal to the height H of the drive bar struts 80. In an example, the height H of the drive bar struts 80 can be less that the outer diameter D of the inner shaft 26 but greater than the inner diameter. In an example, the height H of the drive bar struts 80 can be greater than the outer diameter D of the inner shaft 26 and less than an inner diameter of the outer shaft 28 such that the drive bar 27 can still translate within the outer shaft 28. The inner shaft 26 can include the flexible tab 74 that is configured to flex to allow the drive bar struts 80 to be inserted into a distal opening of the inner shaft 26. Since the height H of the drive bar struts 80 is greater than the inner diameter of the inner shaft 26, the insertion of the drive bar struts 80 causes the flexible tab 74 to flex outward (e.g., away from the longitudinal axis). Once the flexible tab 74 aligns with the recesses 78, the flexible tab 74 moves into the recesses 78 to couple the drive bar struts 80 to the inner shaft 26.

In an example, the top surface 124 of the inner shaft 26 can define slots 79A, 79B, 81, and 84. Slots 79A, 79B, and 81 can be in communication with each other and define the flexible tab 74. Flexible tab 74 can include ridge 195 that, as discussed herein, can be received in both recesses 78 of the drive bar struts 80.

Slot 84 can extend proximally from a distal end of the inner shaft 26. The width of the slot 84 is such that the slot 84 can receive both the drive bar struts 80 and there still is a gap 142 sufficient to receive the blade 32 therein. For example, the gap 142 is such that the blade 32 can freely translate between the drive bar struts 80 without interference from the drive bar struts 80. In one example, the blade facing surfaces 136 can contact the blade 32. In other examples, the blade facing surfaces 136 do not touch the blade 36. Further, as seen in FIG. 7B, no part of the drive bar struts 80 cover the top edge 123 or the bottom edge 125 of the blade 32. That is, when assembled, there is a vertical clearance 190 above and below the blade 32. In one example, vertical clearance 190 indicates that no part of the drive bar is positioned above or below the top and bottom sides of the blade 32. In another example, vertical clearance indicates that there is sufficient room between the top and bottom sides of the blade 32 and a portion of the drive bar. For example, vertical clearance can indicate enough space between the two such that the top and bottom sides of the blade do not come into contact with the drive bar. Thus, in an example, the top, bottom, and side surfaces of the blade 32 are free from contacting the drive bat struts 80. Additionally, in the example shown in FIG. 7B, no part of the drive bar struts 80 extend over the top or bottom side of the blade 32.

The top surface 124 of the inner shaft 26 can also include parallel slots 122A and 122B (collectively referred to as slots 122) located on the flexible tab 74. Recesses 78 have a length that is at least as long as the distance between the proximal end of slot 84 and the distal end of slots 122. Thus, once assembled, the proximal portions 191 of the drive bar struts 80 can be located within slots 122 (e.g., proximal portion 191 of drive bar strut 80A located in slot 122A and proximal portion 191 of drive bar strut 80B located in slot 122B) and the distal portions 192 of drive bar struts 80A and 80B located within slot 84. In the example shown, drive bar struts 80A and 80B do not contact each other.

Figure 6A:
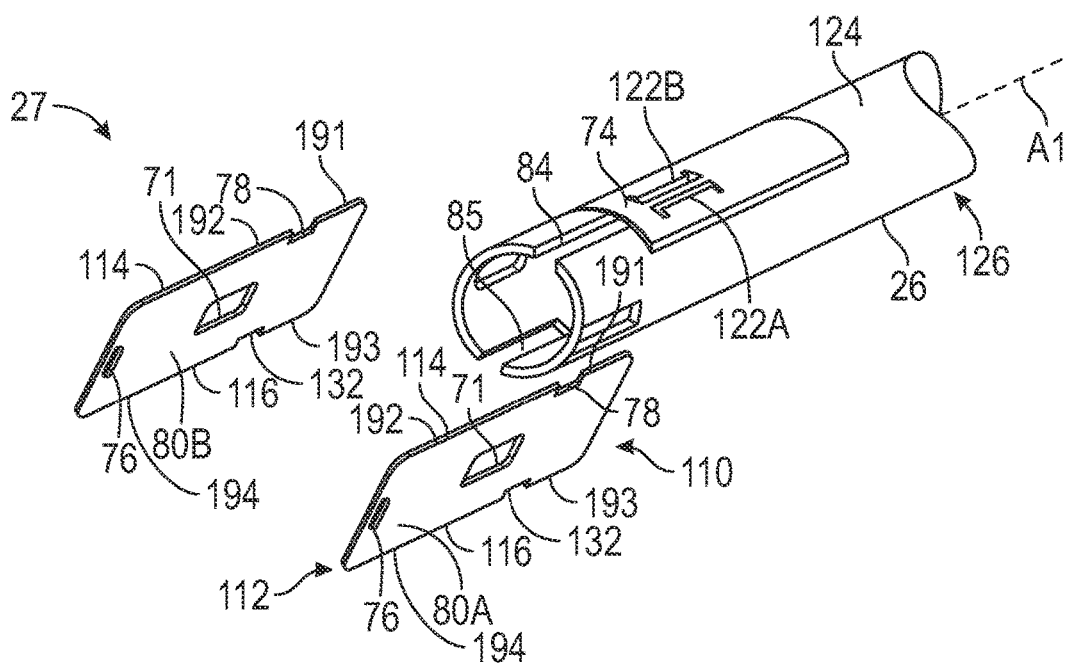
FIG. 6A is an expanded view of the drive bar and the inner shaft, according to an example of the present application.
Figure 6B:
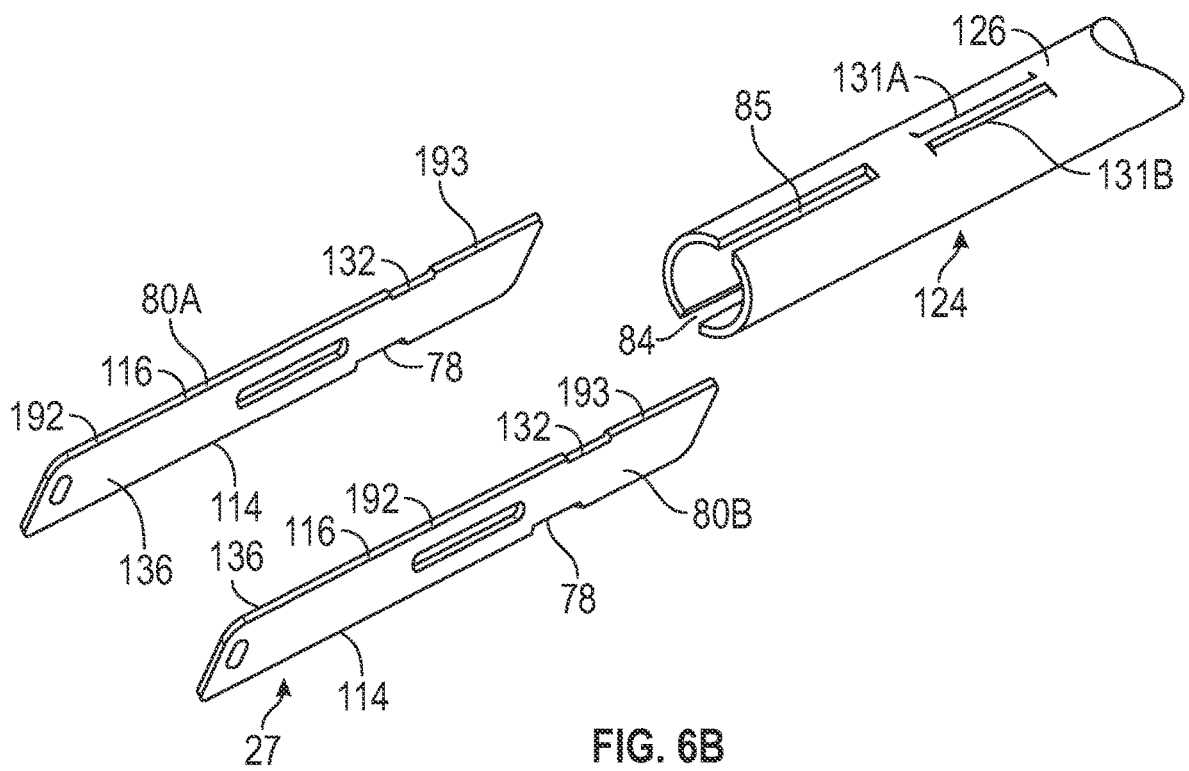
FIG. 6B is an expanded view of the drive bar in FIG. 6A rotated one hundred and eighty (180) degrees.

FIG. 6B illustrates the inner shaft 26 and the drive bar struts 80 in FIG. 6A but rotated 180 degrees. The inner shaft 26 can include slot 85 that can be opposite (diametrically opposed) to slot 84. In one example, a length of slot 85 is different from a length of slot 84. In another example, the lengths of the slots 84 and 85 are the same. As discussed herein regarding slot 84, slot 85 is configured to receive both drive bar struts 80A and 80B. Located proximal to slot 85 is a pair of parallel slots 131A and 131B (collectively referred herein as slots 131). The slots 131 can be opposite slots 122. Thus, once assembled, the proximal portions 193 of the drive bar struts 80 can be located within slots 131 (e.g., proximal portion 193 of drive bar strut 80A located in slot 131A and proximal portion 193 of drive bar strut 80B located in slot 131B) and the distal portions 194 of drive bar struts 80A and 80B located within slot 85. In the example shown, drive bar struts 80A and 80B do not contact each other.

As seen in FIGS. 6A-7B, two identical plates can be used. Therefore, manufacturing the drive bar struts 80 can be simplified. The drive bar struts 80 can be placed facing each other. In an example, the drive bar struts 80 can have interfacing generally parallel spaced inner surface (or blade facing surfaces 136). The drive bar struts 80 can be inserted into the distal end of the inner shaft 26 and simply snap into the inner shaft 26. For example, as the drive bar struts 80 can be inserted into the inner shaft 26 (one at a time or together), the proximal portion 191 of the first edge 114 causes the flexible tab 74 to flex outwardly (away from the longitudinal axis A1) and allow the drive bar struts 80 to be snapped into place within the inner shaft 26.

The features discussed herein on the inner shaft 26 and the drive bar struts 80 are such that the drive bar struts 80 are coupled to the inner shaft 26. However, in an example, once inserted into the inner shaft 26, the drive bar struts 80 can further be coupled to the inner shaft by, e.g., spot welding, soldering, brazing, or other similar process. Additionally, in an example, the drive pin 44 can be secured to the drive bar struts 80, e.g., by spot welding, soldering, brazing, or other similar process.

FIGS. 8-9B illustrate another example of the inner shaft 26 coupled to a drive bar 27'. The example shown can be used with all of the components described herein for forceps 10. The inner shaft 26 is the same inner shaft 26 disclosed herein. However, the drive bar struts 80A and 80B, shown previously, have been modified to drive bar struts 80A' and 80B' (collectively referred to herein as drive bar struts 80').

Drive bar struts 80' are the same as drive bar struts 80 except that they include a different axial track (e.g., axial track 200). As seen in FIG. 8, the axial tracks 200 are defined by a first side 204, a proximal side 207, a second side 206 (opposite the first side 204), and a distal side 208. The drive bar strut 80A' includes a projection 202 extending from the blade facing surface 136 that forms the blade channel configured to receive the blade 32. In the example, shown in FIGS. 8-9B, because the drive bar struts 80' include additional features (e.g., the projection 202), in order to use two identical plates for the drive bar struts 80, the drive bar strut 80B' is drive bar strut 80A' that is rotated one hundred and eighty (180) degrees. Thus, the drive bar strut 80B' includes the projection extending from the blade facing surface 136. Drive bar 27' can be coupled to the inner shaft 26 similarly to how drive bar strut 27 coupled to the inner shaft 26. However, prior to coupling the drive bar 27' to the inner shaft 26, the drive bar struts 80' are positioned around the blade 32 such that the projections 202 extend through the blade track 102 and form an H-beam with the blade 23.

As discussed, drive bar strut 80B is identical to drive bar strut 80A but rotated one hundred eighty (180) degrees. Thus, once assembled, the proximal portion 191 of the drive bar strut 80A can be located within slot 122A and the proximal portion 193 of drive bar strut 80A' can be located within slot 122B and the distal portions 192 and 194 of drive bar struts 80A' and 80B' are located within slot 84. In the example shown, drive bar struts 80A' and 80B' do not contact each other or the blade 32 even as they form an H-beam around the blade 32 with the projections 202 extending within the blade track 102.

As seen in FIG. 9B, the projections 202 extend through the blade track 102 and into the axial track 200 of the other drive bar strut 80'. While the projections 202 extend through the blade track 102, the top and bottom surface of the blade are not covered by any portion of the drive bar struts 80'. In an example, the projections 202 do not extend past the outer surface 210 of the corresponding axial track 200 of the other drive bar strut 80' to maximize the space available for other components within the inner tube 26. Additionally, preventing the projection 202 from extending past the outer surface 210 of the other drive bar strut can assure that the drive bar 27' can extend through an translate the distal plug 48 (see FIG. 4).

Figure 10:
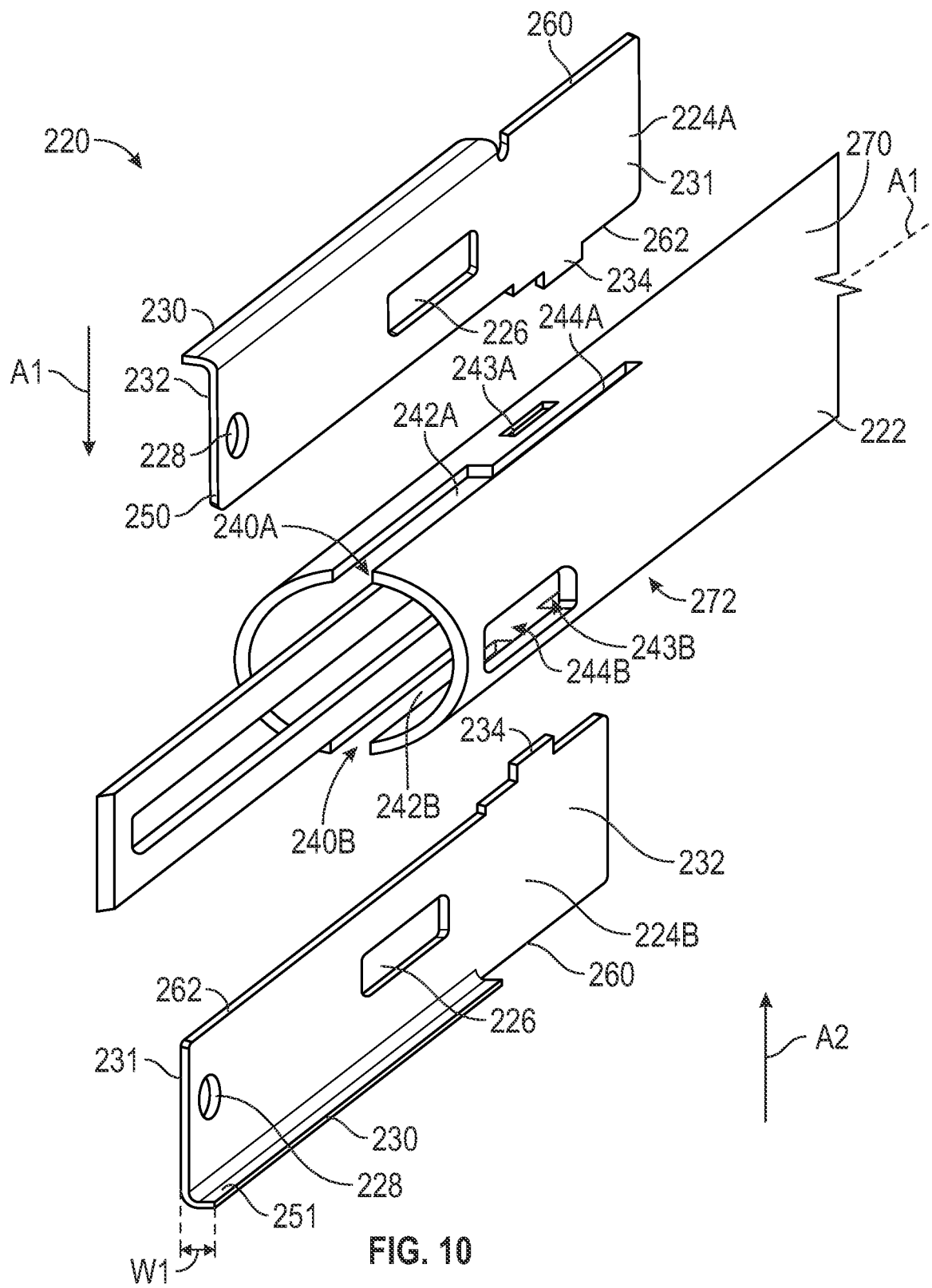
FIG. 10 is an expanded view of a drive bar, an inner shaft, and a blade, according to another example of the present application.
Figure 12:
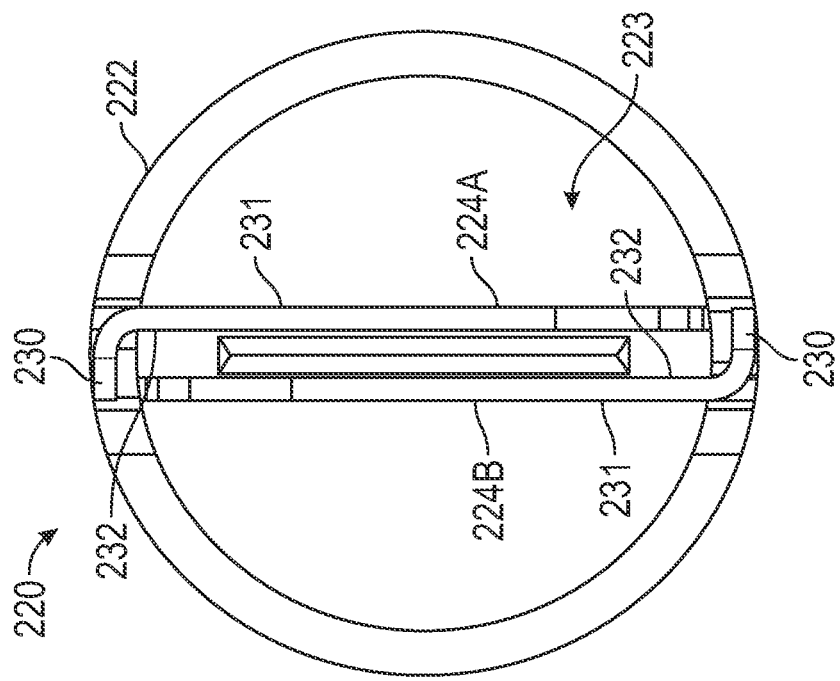
FIG. 12 is a cross-sectional view of the drive bar, the inner shaft, and the blade, according to an example of the present application.
Figure 11:
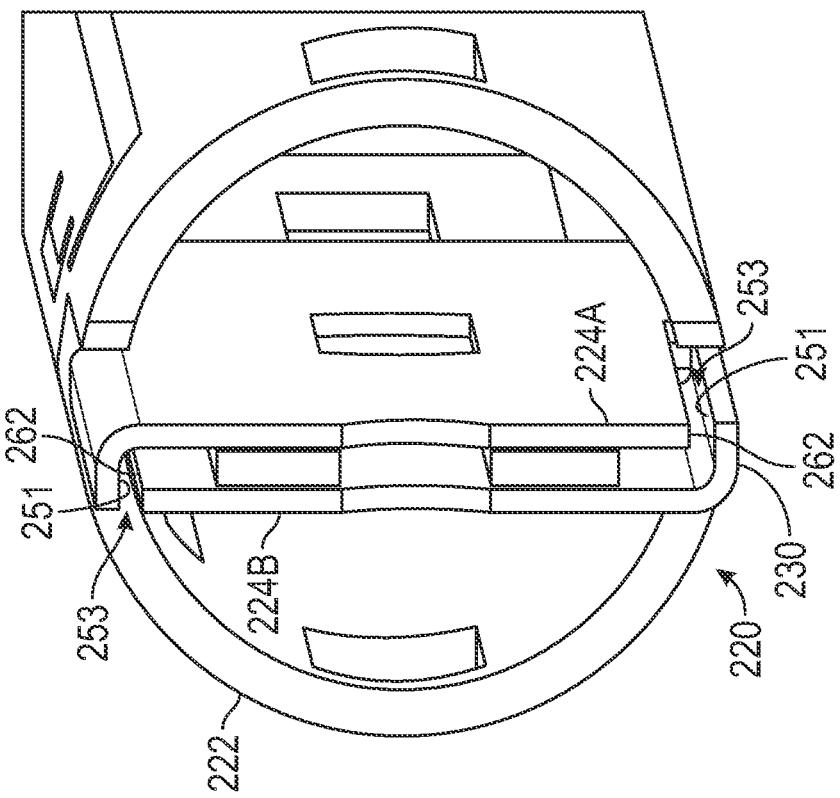
FIG. 11 is a perspective view of the drive bar, the inner shaft, and the blade shown in FIG. 10.

FIGS. 10-12 illustrate another example of a drive bar 220 coupled to an inner shaft 222 that can be used in the forceps 10, as disclosed herein. Drive bar 220 includes a pair of drive bar struts 224A and 224B (collectively drive bar struts 224). In an example, drive bar struts 224A and 224B are identical plates. Drive bar struts 224 include an axial track 226 that can receive the guide 46 and a bore hole 228 that can receive the drive pin 44, as discussed above.

The drive bar struts 224 include a first surface 231, a second surface 232 (opposite the first surface 231), a first edge 260, and a second edge 262. The first and second surfaces 231 and 232 extend between the first edge 260 and the second edge 262. In an example, the drive bar struts 224 have a fold-over projection 230 extending from the first edge 260 away from the second surface 232. That is, the fold-over projection 230 extends substantially perpendicular to the second surface 232. Stated simply, the drive bar struts 224 are L-shaped plates. The fold-over projection 230 forms a short end of the L-shaped plate and the surface extending from the second edge 262 to the fold-over projection 230 forms the long end of the L-shaped plate. The second edge 262 includes a projection 234 extending axially from the longitudinal axis A1. As seen in FIG. 10, drive bar strut 224A and drive bar strut 224B are identical plates. Thus, drive bar strut 224A and drive bar strut 224B are positioned within the inner shaft 26 and drive bar strut 224B is drive bar strut 224A rotated one hundred and eighty (180) degrees.

The inner shaft 222 includes a top surface 270 and a bottom surface 272 and each surface 270, 272 includes slots to receive portions of the drive bar struts 224. In on example, the inner shaft 222 includes slots 240A and 243A (along the top surface 270) and slots 240B and 243B (along the bottom surface 272). Slots 240A and 240B (collectively referred to herein as slots 240) include a first slot portion 242A and 242B (collectively referred to as first slots 242) and a second slot portion 244A and 244B (collectively referred to as second slot portion 244). The first slot portions 242 have a width that is equal to or slightly larger than the width W1 of the projection 230. The second slot portions 244 are thinner than the first slot portions 242. For example, first slot portions 242 receive a portion of the drive bar struts 224 along the first edge 260 that includes the fold-over projection 230. The second slot portions 244 receive the portion of the first edge 260 that does not include the fold-over projection 230. The slots 243A and 243B (collectively referred to as slots 243) are configured to receive respective projections 234 of the drive bar struts 224.

To couple the drive bar 220 to the inner shaft 222, a first drive bar strut 224A and the second drive bar strut 224B will be inserted into slots 240A and 240b. For example, the drive bar strut 224A can be inserted into the slot 240A from the top surface 270 in the direction of arrow A1. The insertion will stop once projection 234 is inserted into slot 243B along the bottom surface 272 of the inner shaft 222. Similarly, the drive bar strut 224B can be inserted into the slot 240B from the bottom surface 272 in the direction of arrow A2. The insertion will stop once projection 234 is inserted into slot 243A along the top surface 270 of the inner shaft 222. As seen in FIGS. 11 and 12, once coupled to the inner shaft 222 a gap 253 is maintained between an under surface 151 of the fold-over projection 230 and the second edge 262. Thus, the drive bar struts 224 are separately coupled to the inner shaft 222. As discuss herein, further coupling methods can be performed. For example, once the drive bar struts 224 are inserted into the inner shaft 222, the coupling can be further enhanced if necessary by, e.g., but not limited to, spot welding the drive bar struts 224 to the inner shaft 222.

Figure 13:
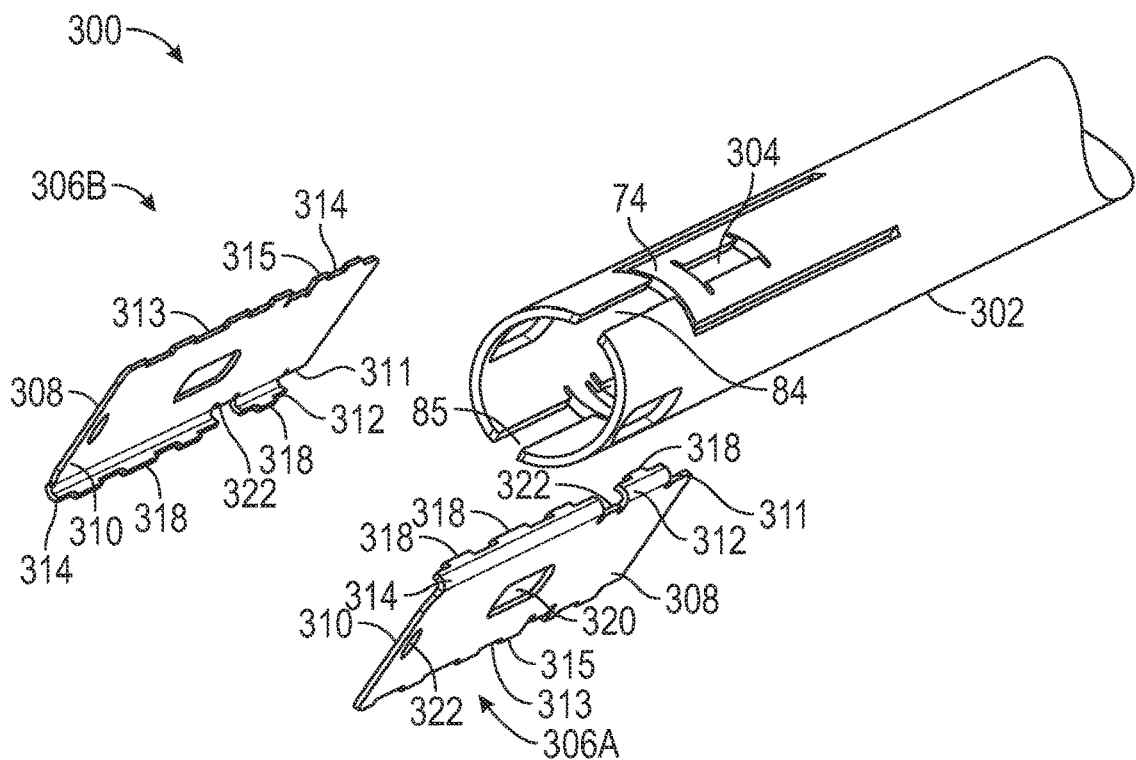
FIG. 13 is an expanded view of a drive bar and an inner shaft, according to another example of the present application.
Figure 14:
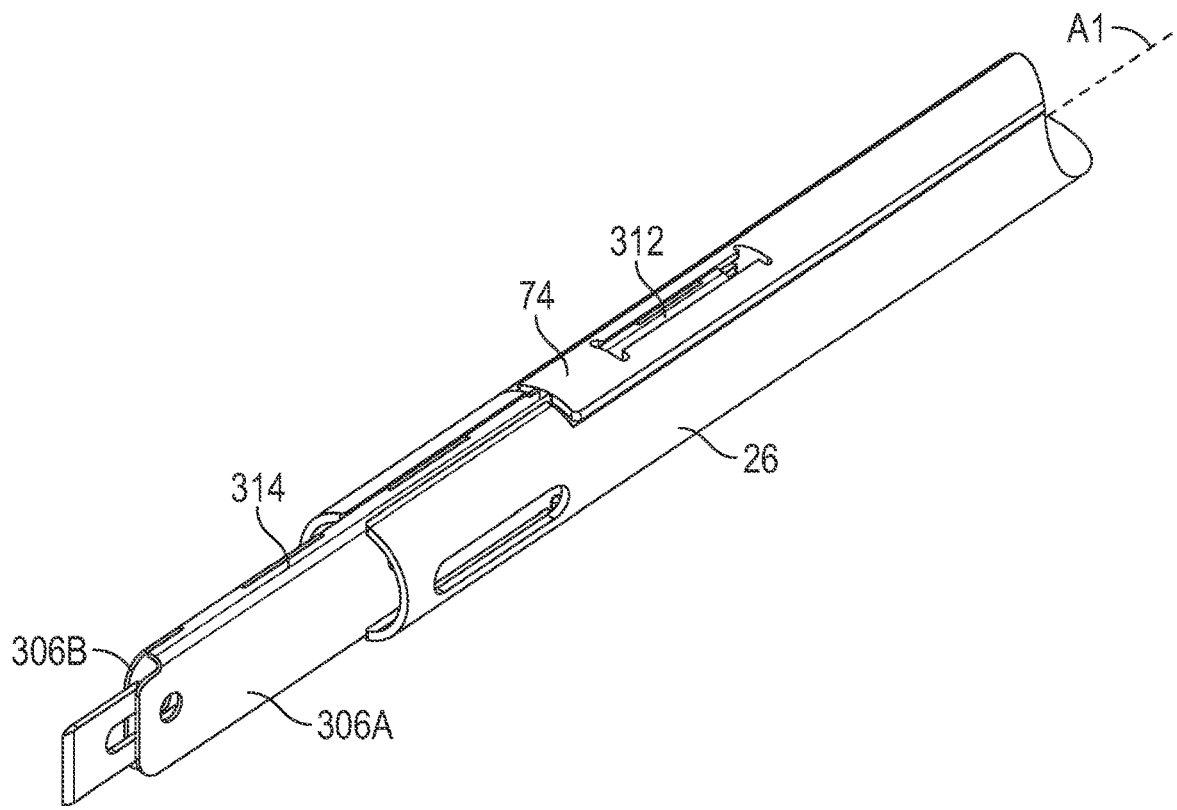
FIG. 14 is a perspective view of the drive bar and the inner shaft shown in FIG. 13 including the blade.
Figure 15:
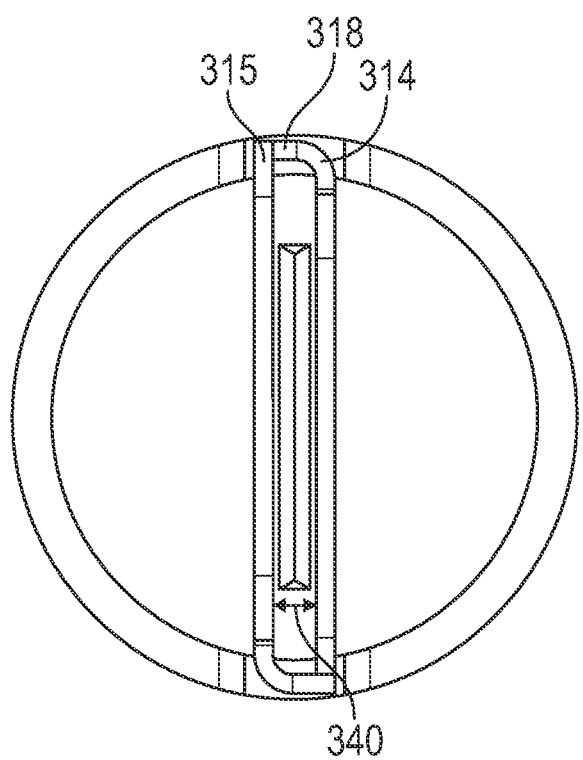
FIG. 15 is a cross-sectional view of the drive bar, the inner shaft, and the blade, according to an example of the present application.

FIGS. 13-14 illustrate another example of a drive bar 300 coupled to an inner shaft 302, that can be used in the forceps 10, as disclosed herein. The example shown in FIGS. 13-14 is most like the example shown in FIGS. 6A-7B; however, in FIGS. 13-14 the drive bar struts 306A and 306B (collectively referred to as drive bar struts 306) are engaged prior to insertion into the inner shaft 302 and the inner shaft 302 includes a single slot 304 on the flexible tab 74 as compared to two slots (122A and 122B) in FIG. 7A. The drive bar struts 306 include the axial track 320 to receive the guide and the bore 322 to receive the drive pin 44, as disclosed herein.

The drive bar struts 306 have a first surface 308, a second surface 310 opposite the first surface 308, a first edge 311, and a second edge 313 opposite the first edge 311, where the first surface 308 and the second surface 310 extend between the first edge 311 and the second edge 313. The first edge 311 includes fold-over projections 312 and 314. In an example, fold-over projection 312 is positioned proximal to recess 322 and fold-over projection 314 is positioned distal to recess 322. Extending from the fold-over projections 312 and 314 are teeth 318. In an example, the fold-over projections 312 and 314 can extend perpendicular or substantially perpendicular to the second surface 310. The second edge 313 include a recess 317 and teeth 315 extending from the second edge 313. That is, teeth 315 can be perpendicular to teeth 318. In one example, the fold over projections 312 and 314 are integral with the drive bar struts 306. In an example, the fold over projections 312 and 314 can be coupled to (e.g., spot welded) to the first edge 311 of the drive bar struts 306.

Prior to coupling the drive bar struts 306 to the inner shaft 302, the two drive bar struts 306 are brought together such that the second faces 310 of each drive bar strut 306 are opposing. For example, drive bar strut 306B is the same drive bar strut 306A, but rotated one hundred and eighty (180) degrees. As the two drive bar struts 306 come together the fold-over projections 312 and 314 maintain the gap 340 between the two drive bar struts 306A and 306B. The two drive bar struts 306A and 306B are engaged when the teeth 318 on the fold-over projection 312 and 314 extend between the teeth 315 on the second edge 313. Once engaged, the drive bar struts 306 can be inserted into the inner tube 26, similar to how drive bar struts 80 are inserted into inner tube 26 (in FIG. 6A-7B), except that in the example shown in FIGS. 13-15, the two drive struts 306 are engaged.

As discussed herein, the drive bar struts 306 can be identical plates. Therefore, manufacturing the drive bar struts 8306 can be simplified. The drive bar struts 306 can be placed facing each other. The drive bar struts 306 can be inserted into the distal end of the inner shaft 302 and simply snap into the inner shaft 302. For example, as the drive bar struts 306 are inserted into the inner shaft 302 (together), the projection 312 causes the flexible tab 74 to flex outwardly (away from the longitudinal axis A1) and allow the drive bar struts 306 to be snapped into place within the inner shaft 26. The fold-over projection 312 and corresponding teeth 315 of the other drive bar strut can be positioned in slot 304. Similarly, the fold-over projection 314 and the corresponding teeth 315 of the other drive bar strut can be positioned in slot 84. In one example, once snapped into place along the inner shaft 24, the drive bar struts 306 can be further coupled (e.g., welded or otherwise) to the inner shaft 26. In another example, the drive bar struts 306 can be coupled (e.g., welded) prior to insertion into the inner shaft. In another example, the drive bar struts 306 can be welded (or otherwise coupled) together and subsequently further coupled (e.g., welded to the inner shaft).

EXAMPLES & VARIOUS NOTES

Each of these non-limiting examples can stand on its own, or can be combined in various permutations or combinations with one or more of the other examples.

Example 1 provides a surgical forceps comprising a drive pin; an outer shaft defining a longitudinal axis; a first jaw pivotably connected to the outer tube, the first jaw including a first set of flanges located at a proximal portion of the first jaw, each flange of the first set of flanges including a first track for receiving the drive pin; a second jaw connected to the outer shaft; an inner shaft located within the outer shaft and extending along the longitudinal axis; and a drive bar coupled to and extending distally from the inner shaft, the drive bar including: a pair of drive bar struts extending from a distal portion of the inner shaft and positioned laterally inward of the first set of flanges, the drive pin securable to the pair of drive bar struts, wherein the drive bar is translatable within the outer shaft to drive the drive pin along the first set of tracks to move the first jaw relative to the second jaw between open and closed positions.

In Example 2, the subject matter of Example 1 optionally includes where each drive bar strut of the pair of drive bar struts includes an opening configured to receive the drive pin, wherein the opening is positioned laterally inward of the outer surface of the inner shaft.

In Example 3, the subject matter of Example 2 optionally includes where the drive bar includes a first pair of axial tracks located proximal to the opening, the first pair of axial tracks arranged to receive a guide therein, the guide secured to the outer shaft.

In Example 4, the subject matter of Examples 1-3 optionally include where inner shaft includes a second pair of axial tracks, the second pair of axial tracks aligned with the first pair of axial tracks and arranged to receive the guide therein.

In Example 5, the subject matter of Examples 1-4 optionally include where the second jaw is pivotably connected to the outer tube, and wherein the second jaw includes a second set of flanges located at a proximal portion of the second jaw, each flange of the second set of flanges including a second track for receiving the drive pin, and wherein the drive bar is translatable within the outer shaft to drive the pin along the first set of tracks and the second set of tracks to move the first jaw and the second jaw between open an closed positioned.

In Example 6, the subject matter of Example 5 optionally includes a blade located within the inner shaft and the drive bar, the blade extending along the longitudinal axis and translatable to extend between the first set of flanges and second set of flanges, the blade including a track configured to receive the drive pin.

In Example 7, the subject matter of Examples 1-6 optionally includes a blade located within the inner shaft and the drive bar, wherein a first edge of the blade and a second edge of the blade do not contact the drive bar.

In Example 8, the subject matter of Examples 1-7 optionally includes a blade located within the inner shaft and the drive bar, wherein a first face of the blade and a second face of the blade do not contact the drive bar.

In Example 9, the subject matter of Examples 1-8 optionally includes where each of the drive bar struts include a projection extending from the first edge of the drive bar struts forming an L-shaped plate.

In Example 10, the subject matter of Examples 1-9 optionally includes where at least one of the drive bar struts include a projection extending from a surface defining a blade channel, such that the projection extends into the blade channel.

In Example 11, the subject matter of Example 10, optionally includes where each of the drive bar struts include the projection extending from the surface defining the blade channel, wherein the drive bar struts form a H-beam, such that the projection of each of the drive bar struts extends into the blade channel.

In Example 12, the subject matter of Examples 1-11 optionally include where the pair of drive bar struts include a first drive bar strut having a first blade channel surface and a second drive bar strut having a second blade channel surface, wherein the first drive bar strut and the second drive bar strut are separately coupled to the inner shaft.

In Example 13, the subject matter of Examples 12 optionally includes where the first drive bar strut and the second drive bar strut are not coupled together.

Example 14 provides a surgical forceps comprising: a drive pin; an outer shaft extending along a longitudinal axis; a first jaw pivotable with respect to the outer shaft, the first jaw including a first set of flanges, each first flange including a first track receiving the drive pin therein; a second jaw connected to the outer shaft and an inner shaft located within the outer shaft and extending along the longitudinal axis; a drive bar coupled to and extending distally from the inner shaft, the drive bar including: a first drive bar strut extending from and separately coupled to the inner shaft; and a second drive bar strut extending from and separately coupled to the inner shaft, the drive pin connected to the first and second drive bar, the drive bar translatable within the outer shaft to translate the drive pin along the first set of tracks to move the first jaw relative to the second jaw between open and closed positions.

In Example 15, the subject matter of Example 14 optionally includes where the second jaw is pivotably connected to the outer tube, and wherein the second jaw includes a second set of flanges located at a proximal portion of the second jaw, each flange of the second set of flanges including a second track for receiving the drive pin, and wherein the drive bar is translatable within the outer shaft to drive the pin along the first set of tracks and the second set of tracks to move the first jaw and the second jaw between open an closed positioned.

In Example 16, the subject matter of Example 15 optionally includes where the drive bar is positioned laterally inward from the first set of flanges and the second set of flanges.

In Example 17, the subject matter of Example 15 optionally includes a blade located within the inner shaft and the drive bar, the blade extending along the longitudinal axis and translatable to extend between the first set of flanges and second set of flanges, the blade including a track configured to receive the drive pin.

In Example 18, the subject matter of Examples 14-17 optionally includes a blade extending along the longitudinal axis and translatable to extend between the first and second jaw, wherein the blade is positioned laterally inward from the first drive bar strut and the second drive bar strut.

In Example 19, the subject matter of Example 18 optionally includes where a first edge of the blade and a second edge of the blade, opposite the first edge, are not covered by a portion of the first drive bar strut and the second drive bar strut.

In Example 20, the subject matter of Examples 14-19 optionally includes where the first edge of the blade and the second edge of the blade do not contact the drive bar.

In Example 21, the subject matter of Example 14-21 optionally includes where a first face of the blade and a second face of the blade do not contact the drive bar.

In Example 22, the subject matter of Examples 14-22 optionally includes where the first drive bar strut is independent from and does not contact the second drive bar strut.

Example 23 provides a surgical forceps comprising: a drive pin; an outer shaft defining a longitudinal axis; a first jaw pivotably connected to the outer tube, the first jaw including a first set of flanges located at a proximal portion of the first jaw, each flange of the first set of flanges including a first track for receiving the drive pin; a second jaw connected to the outer tube; an inner shaft located within the outer shaft and extending along the longitudinal axis; a drive bar coupled to and extending distally from the inner shaft, the drive bar including: a pair of drive bar struts extending from a distal portion of the inner shaft, the drive pin securable to the pair of drive bar struts, wherein the drive bar is translatable within the outer shaft to drive the drive pin along the first set of tracks to move the first jaw relative to the second jaw between open and closed positions; and a blade located within the inner shaft and the drive bar, the blade translatable to extend between the first jaw and the second jaw; wherein each of the drive bar struts include a projection extending from a first edge of the drive bar struts forming an L-shaped plate, and wherein none of a first edge, a second edge, a first face, and a second face of the blade do not contact the drive bar.

In Example 24, the subject matter of Example 23 optionally includes wherein the second jaw is pivotably connected to the outer tube, and wherein the second jaw includes a second set of flanges located at a proximal portion of the second jaw, each flange of the second set of flanges including a second track for receiving the drive pin, and wherein the drive bar is translatable within the outer shaft to drive the pin along the first set of tracks and the second set of tracks to move the first jaw and the second jaw between open an closed positioned.

In Example 25, the subject matter of Examples 23-25 optionally includes where the drive bar is positioned laterally inward from the first set of flanges and the second set of flanges.

Example 26 provides a method of forming a portion of a surgical forceps, the method including: coupling a first drive bar strut to an inner shaft such that a portion of the first drive bar strut extends distally from the inner shaft and coupling a second drive bar strut, separate from the first drive bar strut to the inner shaft such that a portion of the first drive bar strut extends distally form the inner shaft, wherein the first drive bar strut and the second drive bar strut have a distal end that is positioned laterally inward from an outer surface of the inner shaft.

In Example 27, the subject matter of Example 26 optionally includes where coupling the first drive bar strut to the inner shaft and coupling the second drive bar strut to the inner shaft includes: inserting the first drive bar strut into a distal opening of the inner shaft to snap-fit the first drive bar strut to the inner shaft, and inserting the second drive bar strut into the distal opening of the inner shaft to snap-fit the first drive bar strut to the inner shaft.

In Example 28, the subject matter of Examples 26-27 optionally includes coupling the first drive bar strut to the inner shaft and coupling the second drive bar strut to the inner shaft includes: inserting the first drive bar strut into a first axial slot along a top surface of the inner shaft; and inserting the second drive bar strut into a second axial slot along a bottom surface of the inner shaft.

In Example 29, the subject matter of Examples 26-28 optionally includes where the first drive bar strut is identical to the second drive bar strut.

Example 30 is any one or combination of the Examples or elements of the Examples 1-29.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A surgical forceps comprising:

an outer shaft defining a longitudinal axis;
an inner shaft extending through the outer shaft along the longitudinal axis;
an elongate drive bar including:
   first and second drive bar struts each extending through a lumen of the inner shaft along the longitudinal axis and each including an L-shaped cross-sectional profile taken perpendicular to the longitudinal axis; and
   a drive pin connected to the first and second drive bar struts at a distal end of the drive bar; and
a planar blade extending and translatable along the longitudinal axis and arranged between and encompassed by the first and second drive bar struts, including by respective lateral portions of the first and second drive bar struts extending laterally away from the longitudinal axis and laterally away from a plane defined by the blade.

2. The surgical forceps of claim 1, wherein the L-shaped profile is arranged such that:
   the first and second drive bar struts each include a respective shorter lateral fold-over portion bent laterally at an angle away from a respective longer lateral portion; and
   the respective longer lateral portions of the first and second drive bar struts are arranged parallel to each other.

3. The surgical forceps of claim 1, further comprising a jaw assembly including:
   a first jaw pivotably connected to the outer shaft about a pivot point, the first jaw including a first slot sized and shaped to receive the drive pin therethrough; and
   a second jaw connected to the outer shaft.

4. The surgical forceps of claim 3, wherein the drive bar is translatable within the outer shaft to drive the drive pin against the first slot to move the jaw assembly between a first position wherein the first and second jaws are pivotably spaced apart and a second position wherein the first jaw is pivotably moved towards the second jaw.

5. A surgical forceps comprising:
   an outer shaft defining a longitudinal axis;
   an inner shaft extending through the outer shaft along the longitudinal axis;
   a drive bar including:
      first and second drive bar struts each extending through a lumen of the inner shaft along the longitudinal axis and each including an L-shaped profile along their respective lengths, the L-shaped profile being a cross-section of an individual drive bar strut taken perpendicular to the longitudinal axis; and
      a drive pin connected to the first and second drive bar struts at a distal end of the drive bar;
   wherein the L-shaped profile is arranged such that:
      the first and second drive bar struts each include a respective shorter lateral fold-over portion bent laterally at an angle away from a respective longer lateral portion; and
      the respective longer lateral portions of the first and second drive bar struts are arranged parallel to each other;
   a jaw assembly including:
      a first jaw pivotably connected to the outer shaft about a pivot point, the first jaw including a first slot sized and shaped to receive the drive pin therethrough; and
      a second jaw connected to the outer shaft; and
   a blade extending through the drive bar along the longitudinal axis and arranged between the first and second drive bar struts and parallel to the respective longer lateral portions of the first and second drive bar struts, wherein the blade is translatable to extend distally out of the inner shaft and beyond the pivot point of the first jaw;
   wherein the drive bar is translatable within the outer shaft to drive the drive pin against the first slot to move the jaw assembly between a first position wherein the first and second jaws are pivotably spaced apart and a second position wherein the first jaw is pivotably moved towards the second jaw.

6. The surgical forceps of claim 5, wherein:
   the second jaw is pivotably connected to the outer shaft about the pivot point;
   the second jaw includes a second slot sized and shaped to receive the drive pin therethrough; and
   the drive bar is translatable within the outer shaft to drive the drive pin against both the first slot and the second slot to respectively move the first jaw and the second jaw between the first position and second position wherein the first and second jaws are pivotably moved towards the each other.

7. The surgical forceps of claim 6, wherein lateral translation of the drive bar against the first slot and the second slot concurrently pivots the first jaw and the second jaw about the pivot point and towards each other.

8. The surgical forceps of claim 5, wherein the first and second drive bar struts each include a respective drive pin opening sized and shaped to receive the drive pin therethrough and a respective axial track positioned proximal to the corresponding respective drive pin opening, wherein a cross-sectional area defined by each respective drive pin opening is smaller than a cross-sectional area defined by its corresponding respective axial track.

9. The surgical forceps of claim 5, wherein the inner shaft includes a first pair of mating features sized and shaped to respectively receive the respective shorter lateral fold-over portions of the first and second drive bar struts and to mate therewith.

10. The surgical forceps of claim 9, wherein the inner shaft includes a second pair of mating features sized and shaped to respectively receive the respective longer lateral portions of the first and second drive bar struts.

11. The surgical forceps of claim 5, wherein the first and second drive bar struts confine the blade on either side to limit rotation of the blade about the longitudinal axis and to restrict longitudinal travel of the blade to a plane parallel to blade-facing surfaces of the respective longer lateral portions of the first and second drive bar struts.

12. The surgical forceps of claim 5, wherein the first and second drive bar struts are arranged within the inner shaft such that the struts do not contact each other.

13. The surgical forceps of claim 5, wherein the first and second drive bar struts are arranged within the inner shaft such that the shorter lateral fold-over portion of the first drive bar strut contacts the longer lateral portion of the second drive bar strut and the shorter lateral fold-over portion of the second drive bar strut contacts the longer lateral portion of the first drive bar strut.

14. The surgical forceps of claim 5, wherein the first and second drive bar struts each include a respective shorter lateral fold-over portion bent laterally at a substantially perpendicular angle away from a respective longer lateral portion, and the respective shorter lateral fold-over portions of the first and second drive bar struts are arranged parallel to each other.

15. The surgical forceps of claim 5, wherein the first and second drive bar struts are superimposable with each other, and the first drive bar strut is arranged opposite the second drive bar strut about the longitudinal axis at an angle between 175 degrees and 195 degrees relative to the second drive bar strut.

16. The surgical forceps of claim 5, wherein the respective shorter lateral fold-over portions project from their corresponding respective longer lateral portions along a first distal longitudinal section of the respective drive bar strut, and wherein the respective shorter lateral fold-over portions do not project from their corresponding respective longer lateral portions along a second proximal longitudinal section of the respective drive bar strut.

17. A surgical forceps comprising:
   a drive pin;
   an outer shaft defining a longitudinal axis;
   a first jaw pivotably connected to the outer shaft, the first jaw including a first set of flanges located at a proximal portion of the first jaw, each flange of the first set of flanges including a first track for receiving the drive pin;
   a second jaw connected to the outer shaft;
   an inner shaft located within the outer shaft and extending along the longitudinal axis;
   a drive bar coupled to and extending distally from the inner shaft, the drive bar including:
      a pair of drive bar struts extending longitudinally through a lumen of the inner shaft from a distal portion of the inner shaft, the drive pin securable to the pair of drive bar struts, wherein the drive bar is translatable within the outer shaft to drive the drive pin along the set of first tracks to move the first jaw relative to the second jaw between open and closed positions; and
   a blade located within the inner shaft and the drive bar, the blade translatable to extend between the first jaw and the second jaw,
   wherein an individual one of the drive bar struts includes a flange defining a plane that is bent laterally at an angle away from and intersecting a plane defined by the drive bar strut and, wherein the flange is also bent laterally at an angle away from the blade.

18. The surgical forceps of claim 17, wherein the second jaw is pivotably connected to the outer shaft, and wherein the second jaw includes a second set of flanges located at a proximal portion of the second jaw, each flange of the second set of flanges including a second track for receiving the drive pin, and wherein the drive bar is translatable within the outer shaft to drive the pin along the set of first tracks and the set of second tracks to move the first jaw and the second jaw between open an closed positioned.

19. The surgical forceps of claim 17, wherein the drive bar is positioned laterally inward from the first set of flanges and the second set of flanges.

* * * * *